(12) United States Patent  (10) Patent No.: US 9,144,397 B2
Naimi et al.  (45) Date of Patent: Sep. 29, 2015

(54) METHOD APPARATUS AND SYSTEM FOR DETERMINING A THERMAL SIGNATURE

(75) Inventors: Eyal Naimi, Jerusalem (IL); Eddy Solomon, RaAnana (IL); Israel Boaz Arnon, Halamish (IL)

(73) Assignee: Real Imaging Ltd., Lod (IL)

( * ) Notice: Subject to any disclaimer, the term of this patent is extended or adjusted under 35 U.S.C. 154(b) by 414 days.

(21) Appl. No.: 13/132,332

(22) PCT Filed: Dec. 3, 2009

(86) PCT No.: PCT/IL2009/001149
§ 371 (c)(1),
(2), (4) Date: Jun. 2, 2011

(87) PCT Pub. No.: WO2010/064249
PCT Pub. Date: Jun. 10, 2010

(65) Prior Publication Data
US 2011/0243409 A1    Oct. 6, 2011

Related U.S. Application Data

(60) Provisional application No. 61/193,504, filed on Dec. 4, 2008.

(51) Int. Cl.
G06K 9/00 (2006.01)
A61B 5/107 (2006.01)
A61B 5/00 (2006.01)

(52) U.S. Cl.
CPC ............. *A61B 5/1077* (2013.01); *A61B 5/0064* (2013.01)

(58) Field of Classification Search
None
See application file for complete search history.

(56) References Cited

U.S. PATENT DOCUMENTS

| 5,941,832 A | * | 8/1999 | Tumey et al. | 600/549 |
| 5,961,466 A | | 10/1999 | Anbar | |
| 6,317,617 B1 | * | 11/2001 | Gilhuijs et al. | 600/408 |
| 6,442,419 B1 | | 8/2002 | Chu et al. | |
| 6,529,617 B1 | * | 3/2003 | Prokoski | 382/128 |
| 6,684,097 B1 | * | 1/2004 | Parel et al. | 600/427 |
| 6,757,412 B1 | * | 6/2004 | Parsons et al. | 382/128 |
| 6,850,862 B1 | | 2/2005 | Chidichimo et al. | |
| 6,950,693 B1 | * | 9/2005 | Wehberg | 600/476 |

(Continued)

FOREIGN PATENT DOCUMENTS

DE    10150918 A1 * 5/2003
WO   WO 2006/003658   1/2006

(Continued)

OTHER PUBLICATIONS

Srirang Manohar,Alexei Kharine,Johan C. G. van Hespen,Wiendelt Steenbergen,Ton G. van Leeuwen; "Photoacoustic mammography laboratory prototype: imaging of breast tissue phantoms;" 2004, Journal of Biomedical Optics, vol. 9 No. 6.*

(Continued)

*Primary Examiner* — Bhavesh Mehta
*Assistant Examiner* — Oneal R Mistry

(57) ABSTRACT

A method of determining a thermal signature from thermal data associated with a body section is disclosed. The method comprises: segmenting the thermal data into a plurality of segments, and calculating a set of locations defining a contour, each location being central with respect to picture-elements associated with one segment, thereby determining the thermal signature based on the contour.

15 Claims, 43 Drawing Sheets
(10 of 43 Drawing Sheet(s) Filed in Color)

(56) References Cited

U.S. PATENT DOCUMENTS

| | | | |
|---|---|---|---|
| 6,990,239 B1 * | 1/2006 | Nelson | 382/224 |
| 6,996,256 B2 * | 2/2006 | Pavlidis | 382/118 |
| 7,072,504 B2 | 7/2006 | Miyano et al. | |
| 7,120,292 B2 * | 10/2006 | Kunii et al. | 382/159 |
| 7,292,719 B2 | 11/2007 | Arnon | |
| 7,327,860 B2 * | 2/2008 | Derakhshani et al. | 382/117 |
| 7,388,974 B2 * | 6/2008 | Yanagita | 382/128 |
| 7,394,085 B2 * | 7/2008 | Shikii et al. | 250/583 |
| 7,406,184 B2 * | 7/2008 | Wolff et al. | 382/118 |
| 7,408,156 B2 * | 8/2008 | Yannacone et al. | 250/332 |
| 7,485,096 B2 * | 2/2009 | Mitra | 600/549 |
| 7,490,085 B2 * | 2/2009 | Walker et al. | 1/1 |
| 7,496,219 B2 * | 2/2009 | Okada | 382/128 |
| 7,639,842 B2 * | 12/2009 | Kelle et al. | 382/109 |
| 7,668,358 B2 * | 2/2010 | Snoeren et al. | 382/131 |
| 7,736,313 B2 * | 6/2010 | Luo et al. | 600/437 |
| 7,738,683 B2 * | 6/2010 | Cahill et al. | 382/128 |
| 7,747,055 B1 * | 6/2010 | Vining et al. | 382/131 |
| 7,756,317 B2 * | 7/2010 | Huo et al. | 382/132 |
| 7,865,002 B2 * | 1/2011 | Basilico et al. | 382/128 |
| 7,871,406 B2 * | 1/2011 | Nields et al. | 606/27 |
| 7,899,225 B2 * | 3/2011 | Collins et al. | 382/128 |
| 7,962,187 B2 * | 6/2011 | Fantini | 600/310 |
| 8,073,214 B2 * | 12/2011 | Hong et al. | 382/128 |
| 2001/0046316 A1 | 11/2001 | Miyano et al. | |
| 2004/0037465 A1 * | 2/2004 | Krause | 382/199 |
| 2006/0062448 A1 * | 3/2006 | Hirsch et al. | 382/154 |
| 2007/0133852 A1 * | 6/2007 | Collins et al. | 382/128 |
| 2008/0077019 A1 * | 3/2008 | Xiao et al. | 600/474 |
| 2008/0298642 A1 * | 12/2008 | Meenen | 382/115 |

FOREIGN PATENT DOCUMENTS

| | | |
|---|---|---|
| WO | WO 2008/130905 | 10/2008 |
| WO | WO 2009125887 A1 * | 10/2009 |
| WO | WO 2010/064249 | 6/2010 |

OTHER PUBLICATIONS

Srirang Manohar et al. "Photoacoustic mammography laboratory prototype: imaging of breast tissue phantoms" Journal of Biomedical Optics , 1172-1181. Dec. 2004, hereinafter Manohar.*

International Preliminary Report on Patentability Dated Jun. 16, 2011 From the International Bureau of WIPO Re. Application No. PCT/IL2009/001149.

International Search Report and the Written Opinion Dated May 25, 2010 From the International Searching Authority Re.: Application No. PCT/IL2009/001149.

Office Action Dated Apr. 11, 2013 From the Israel Patent Office Re. Application No. 213326 and Its Translation Into English.

* cited by examiner

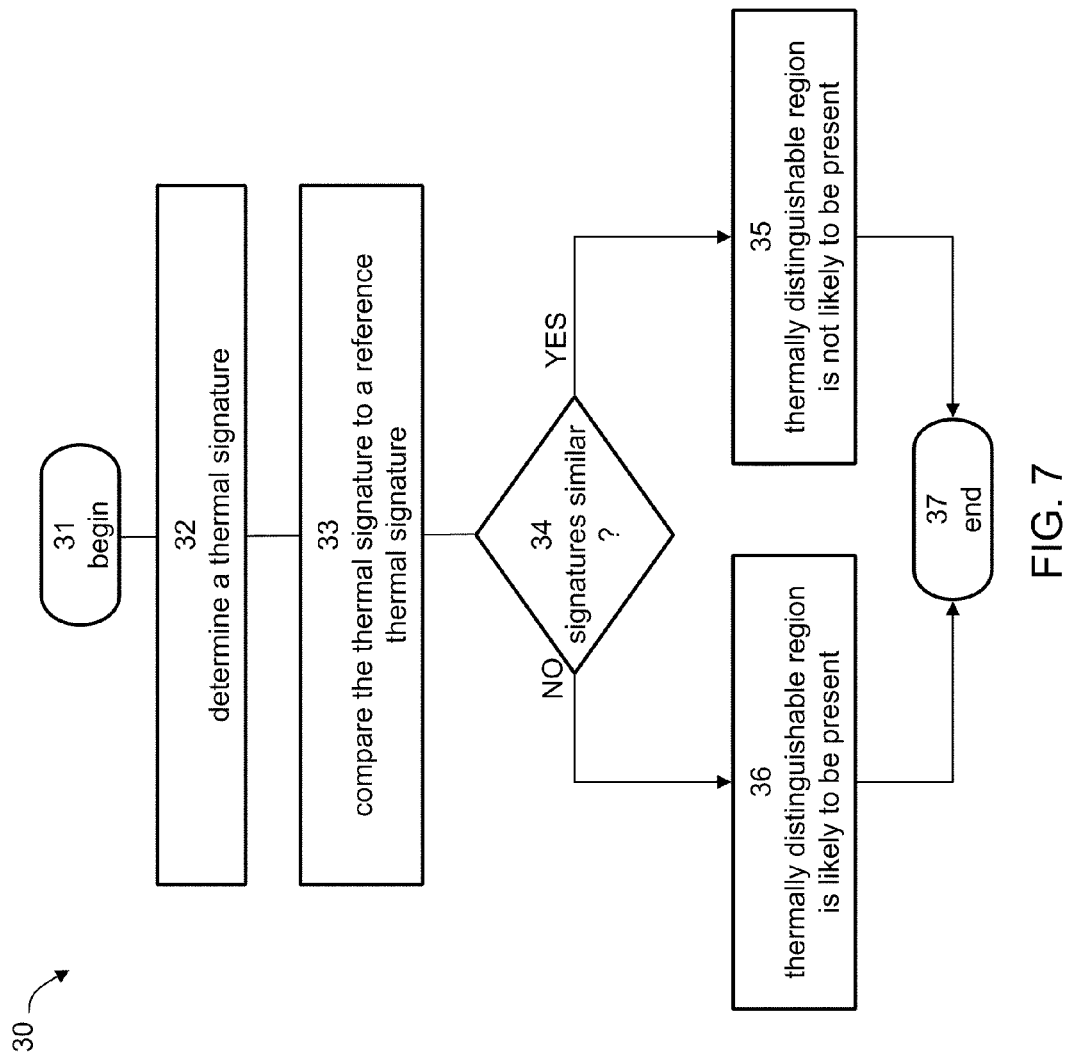

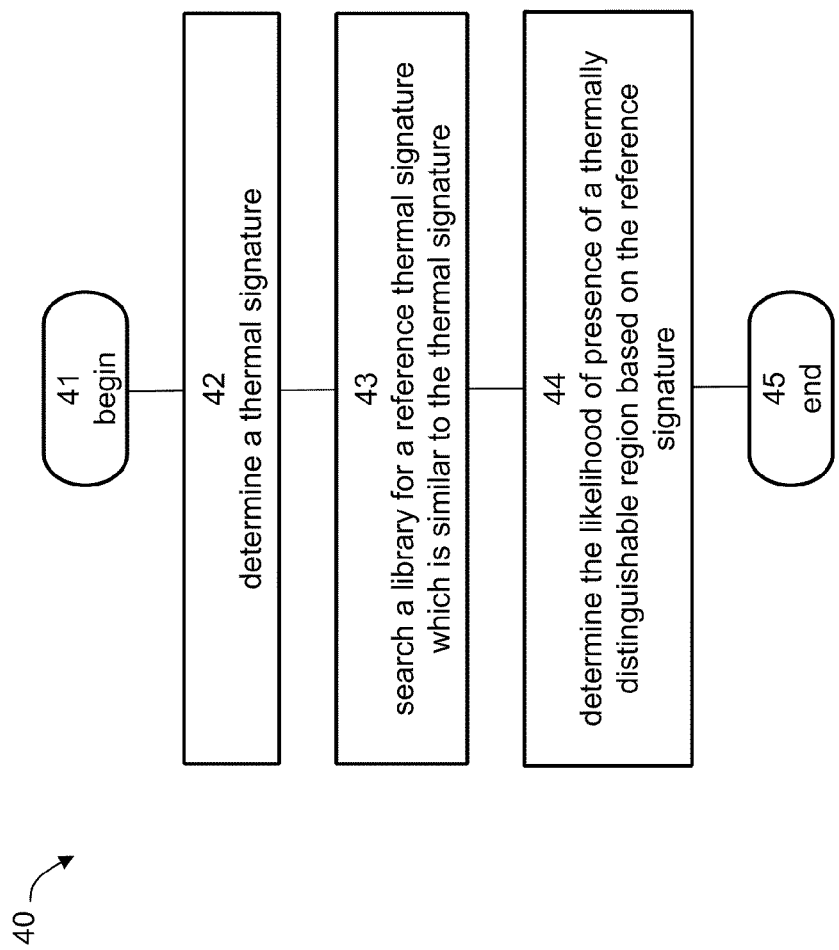

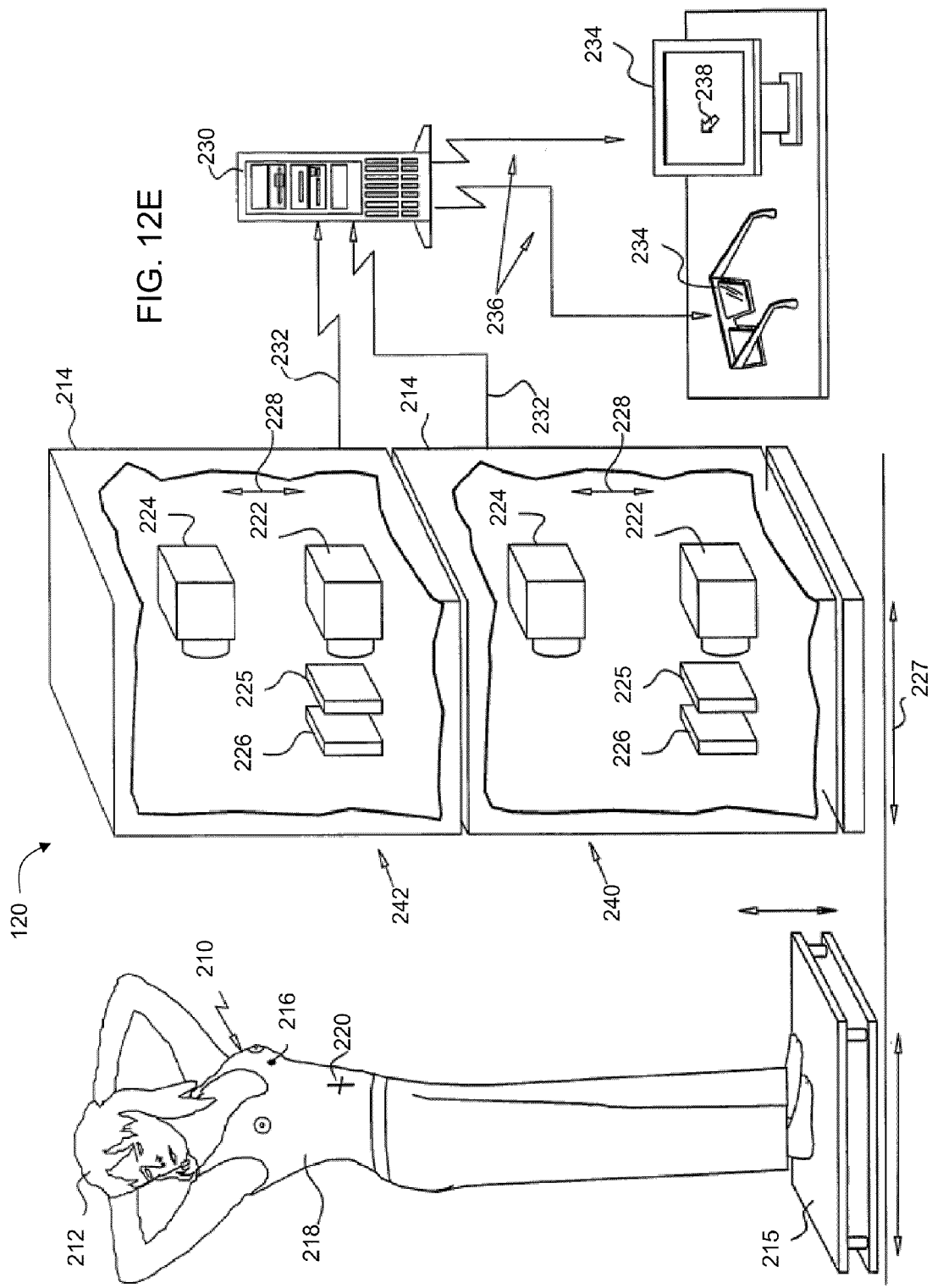

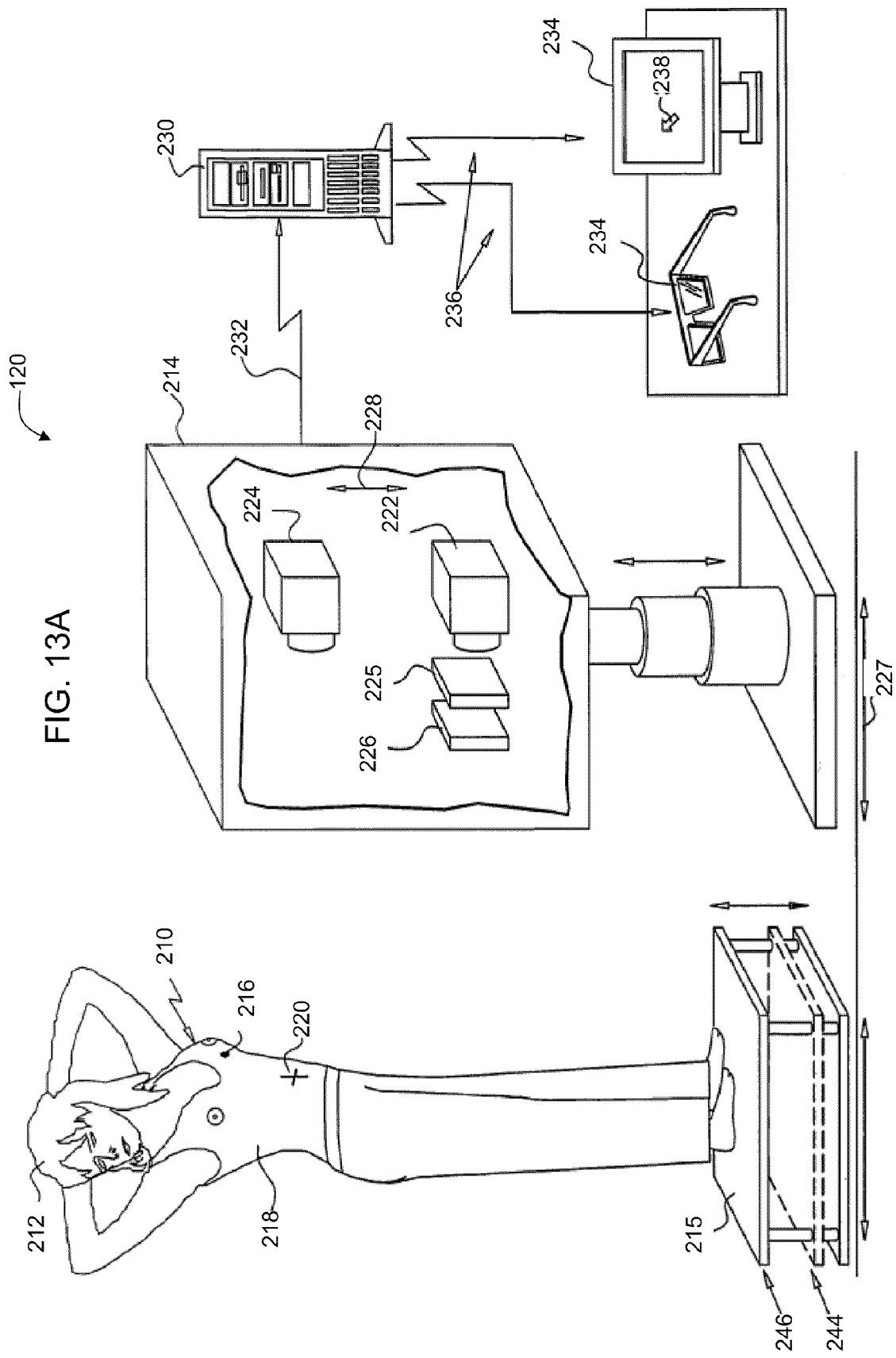

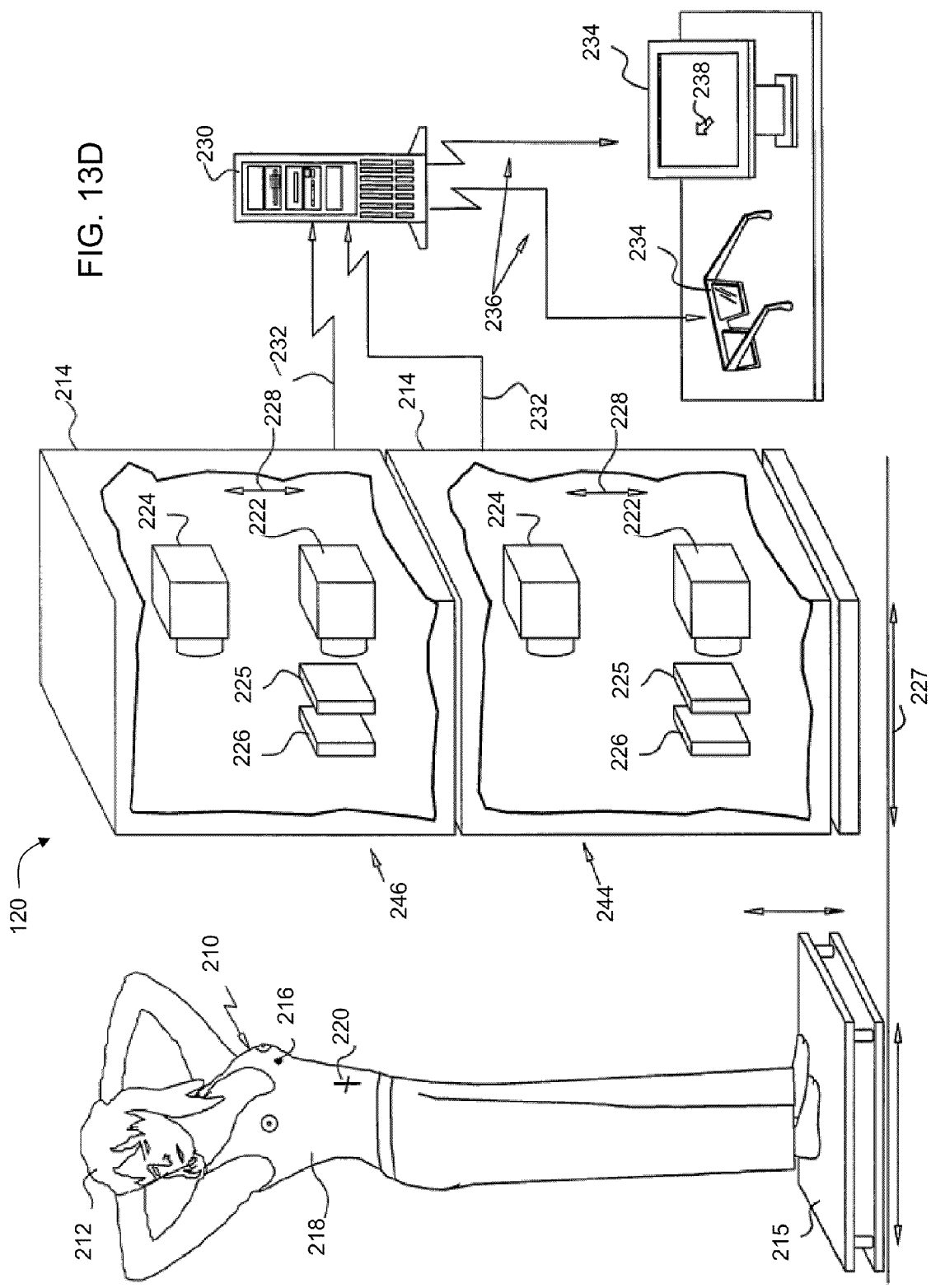

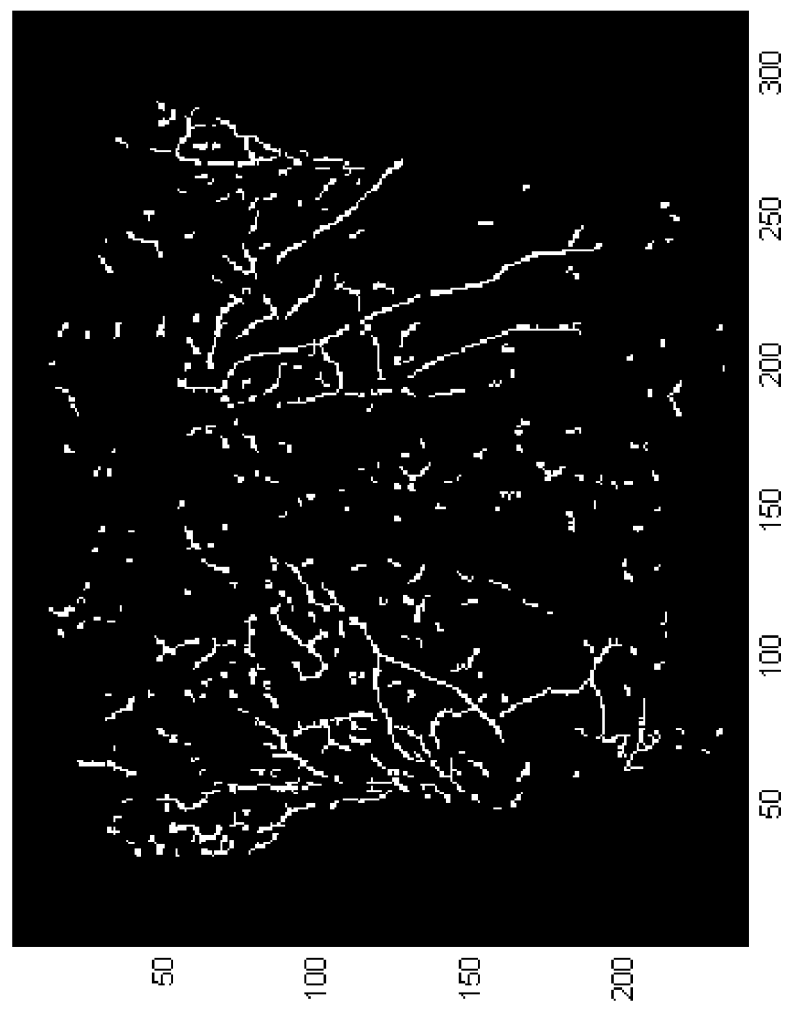
FIG. 16-I

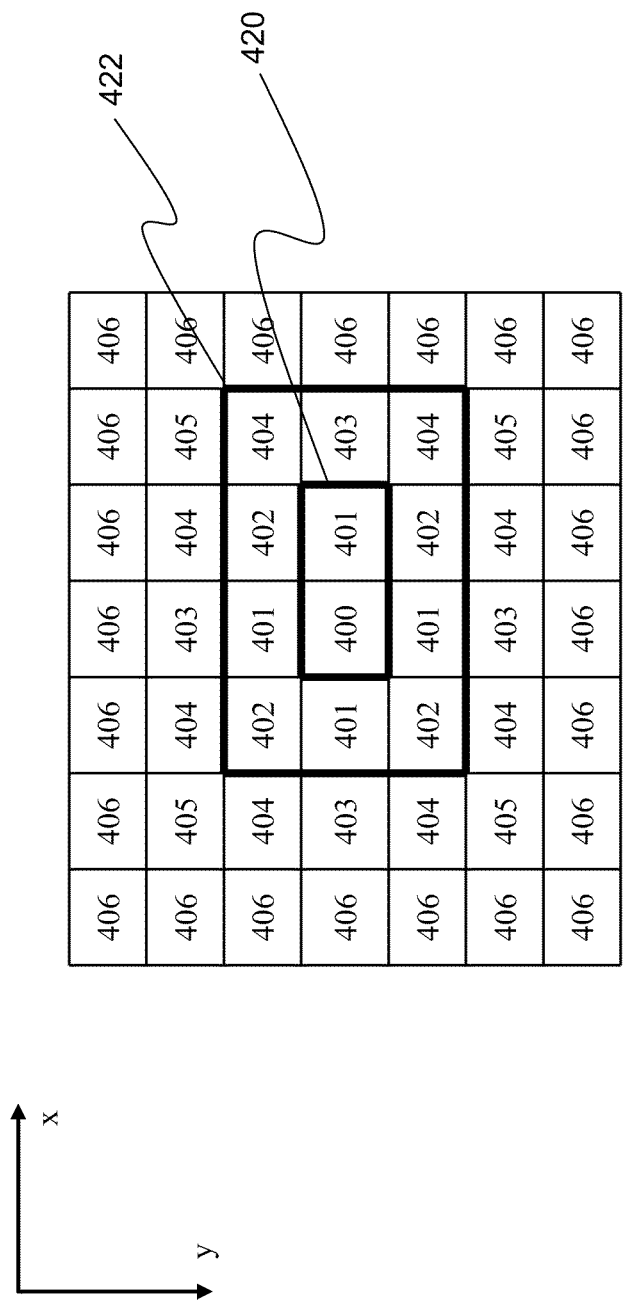

METHOD APPARATUS AND SYSTEM FOR DETERMINING A THERMAL SIGNATURE

RELATED APPLICATIONS

This application is a National Phase of PCT Patent Application No. PCT/IL2009/001149 having International filing date of Dec. 3, 2009, which claims the benefit of priority of U.S. Provisional Patent Application No. 61/193,504 filed on Dec. 4, 2008. The contents of the above applications are all incorporated herein by reference.

FIELD AND BACKGROUND OF THE INVENTION

The present invention, in some embodiments thereof, relates to thermal images and, more particularly, but not exclusively, to the analysis of thermal images by determining a thermal signature within the images.

The use of imaging in diagnostic medicine dates back to the early 1900s. Presently there are numerous different imaging modalities at the disposal of a physician allowing imaging of hard and soft tissues and characterization of both normal and pathological tissues.

Infra red imaging is utilized for characterizing a thermally distinguishable site in a human body for the purposes of identifying inflammation. Infrared cameras produce two-dimensional images known as thermographic images. A thermographic image is typically obtained by receiving from the body of the subject radiation at any one of several infrared wavelength ranges and analyzing the radiation to provide a two-dimensional temperature map of the surface. The thermographic image can be in the form of either or both of a visual image and corresponding temperature data. The output from infrared cameras used for infrared thermography typically provides an image comprising a plurality of pixel data points, each pixel providing temperature information which is visually displayed, using a color code or grayscale code. The temperature information can be further processed by computer software to generate for example, mean temperature for the image, or a discrete area of the image, by averaging temperature data associated with all the pixels or a sub-collection thereof.

Based on the thermographic image, a physician diagnoses the site, and determines, for example, whether or not the site includes an inflammation while relying heavily on experience and intuition.

U.S. Pat. No. 7,072,504 discloses an approach which utilizes two infrared cameras (left and right) in combination with two visible light cameras (left and right). The infrared cameras are used to provide a three-dimensional thermographic image and the visible light cameras are used to provide a three-dimensional visible light image. The three-dimensional thermographic and three-dimensional visible light images are displayed to the user in an overlapping manner.

International Patent Publication No. 2006/003658, the contents of which are hereby incorporated by reference, discloses a system which includes non-thermographic image data acquisition functionality and thermographic image data acquisition functionality. The non-thermographic image data acquisition functionality acquires non-thermographic image data, and the thermographic image data acquisition functionality acquires thermographic image data.

U.S. Pat. No. 7,292,719, the contents of which are hereby incorporated by reference discloses a system for determining presence or absence of one or more thermally distinguishable objects in a living body. A combined image generator configured combines non-thermographic three-dimensional data of a three-dimensional tissue region in the living body with thermographic two-dimensional data of the tissue region so as to generate three-dimensional temperature data associated with the three-dimensional tissue region.

Also of interest is U.S. Pat. No. 6,442,419 disclosing a scanning system including an infrared detecting mechanism which performs a 360° data extraction from an object, and a signal decoding mechanism, which receives electrical signal from the infrared detecting mechanism and integrates the signal into data of a three-dimensional profile curved surface and a corresponding temperature distribution of the object.

Additional background art includes U.S. Pat. No. 6,850,862 which discloses the generation of three-dimensional maps of temperature distribution, and U.S. Pat. No. 5,961,466 which discloses detection of breast cancer from a rapid time series of infrared images which is analyzed to detect changes in the distribution of thermoregulatory frequencies over different areas of the skin.

SUMMARY OF THE INVENTION

According to an aspect of some embodiments of the present invention there is provided a method of determining a thermal signature from thermal data associated with a body section, the thermal data being arranged gridwise in a plurality of picture-elements representing a thermal image, the method comprising: segmenting the thermal data into a plurality of segments; and calculating a set of locations defining a contour, each location being central with respect to picture-elements associated with one segment; thereby determining the thermal signature based on the contour.

According to an aspect of some embodiments of the present invention there is provided a method of determining presence or absence of a thermally distinguished region in a body section, comprising: determining a thermal signature of the body section as described above, and comparing the thermal signature with a reference thermal signature so as to determine the presence or absence of the thermally distinguished region.

According to an aspect of some embodiments of the present invention there is provided a method of determining presence or absence of a thermally distinguished region in a body section, comprising: determining a thermal signature of the body section as described above; and employing a comparison procedure for searching a library of reference thermal signatures for a reference thermal signature similar to the thermal signature of the body section so as to determine the presence or absence of the thermally distinguished region.

According to an aspect of some embodiments of the present invention there is provided a method of monitoring evolution of a thermally distinguished region in a body section, comprising: obtaining a series of thermal images of the body section; for each thermal image, determining a thermal signature of the body section as described above; and comparing at least two of the thermal signatures, and using the comparison for assessing changes in the thermally distinguished region, thereby monitoring the evolution of the thermally distinguished region.

According to an aspect of some embodiments of the present invention there is provided a method of monitoring evolution of a thermally distinguished region in a body section having a surface, comprising: generating a series of thermospatial representations of the body section, each representation having thermal data of the body section associated with spatial data representing the surface; for each thermospatial representation, determining a thermal signature of the body section as described above; and comparing at least two of the thermal signatures, and using the comparison for assessing changes in the thermally distinguished region, thereby monitoring the evolution of the thermally distinguished region.

According to an aspect of some embodiments of the present invention there is provided a method of comparing a thermospatial representation of a body section with a reference thermospatial representation of a reference body section, each thermospatial representation having thermal data of a respective body section associated with spatial data describing a surface of the respective body section, the method comprising: for each thermospatial representation, segmenting the thermal data into a plurality of segments, and determining a morphology associated with at least one of the segments based on the thermal data of the thermospatial representation; comparing respective morphologies amongst the thermospatial representations; and using the comparison for determining the presence or absence of a thermally distinguished region in the body section.

According to some embodiments of the present invention the thermally distinguished region is a tumor and the method further comprises applying a destructive treatment to the tumor, wherein the comparison is used for assessing whether the size of the tumor is stable.

According to some embodiments of the present invention the comparison comprises contour alignment.

According to some embodiments of the present invention the method further comprises assigning weights for at least some picture-elements of the spatial data, wherein the calculation of the set of locations is based on the weights.

According to some embodiments of the invention the assignment of weights comprises performing spatial derivatives.

According to some embodiments of the invention the method further comprises defining a region-of-interest within the body section wherein the calculation of the set is performed only over the region-of-interest.

According to some embodiments of the invention the spatial data comprises data representing a surface of tissue being nearby to the body section and the method comprises defining a spatial boundary between the surface of the body section and the surface of the nearby tissue.

According to an aspect of some embodiments of the present invention there is provided apparatus for determining a thermal signature from thermal data associated with a body section, the thermal data being arranged gridwise in a plurality of picture-elements representing a thermal image, the apparatus comprising: a segmentation unit, for segmenting the thermal data into a plurality of segments; a location calculator, for calculating a set of locations defining a contour, each location being central with respect to picture-elements associated with one segment.

According to some embodiments of the invention the thermal data is associated with spatial data describing a surface of the body section, hence forming, together with the spatial data a thermospatial representation of the body section, and wherein at least one location of the set represents a volume-element.

According to an aspect of some embodiments of the present invention there is provided an imaging and processing system, comprising: a thermospatial imaging system operable to provide a thermospatial representation of a body section having a surface, the thermospatial representation having thermal data of the body section associated with spatial data describing the surface; and the apparatus for determining a thermal signature.

According to some embodiments of the present invention the apparatus further comprises a weights assigner for assigning weights for at least some picture-elements, and wherein the location calculator is operable to calculate the set of locations based on the weights.

According to some embodiments of the invention the weights assigner is operable to employ an edge detection procedure.

According to some embodiments of the invention each location is a weighted average of picture-element associated with one segment.

According to some embodiments of the present invention the apparatus further comprises an analysis unit operable to compare the thermal signature with a reference thermal signature.

According to some embodiments of the invention the analysis unit is configured for employing a comparison procedure and accessing a library of thermal signatures for searching the library for a reference thermal signature similar to the thermal signature of the body section.

According to some embodiments of the present invention the analysis unit is operable to employ contour alignment for the comparison.

According to some embodiments of the present invention the spatial data comprises data representing a surface of tissue being nearby to the body section and the apparatus comprises a boundary definition unit for defining a spatial boundary between the surface of the body section and the surface of the nearby tissue.

According to some embodiments of the present invention the contour is planar.

According to some embodiments of the present invention the contour is non-planar.

According to some embodiments of the present invention the the contour is branched.

According to some embodiments of the present invention the the contour is non-branched.

According to some embodiments of the present invention the the contour is continuous.

According to some embodiments of the present invention the the contour is discontinuous.

According to some embodiments of the present invention the reference thermal signature corresponds to a reference body section other than the body section and being similar in shape thereto.

According to some embodiments of the present invention the reference thermal signature comprises history data of the body section.

According to some embodiments of the present invention the body section is a first breast of a subject and the reference body section is a second breast of the subject.

According to an aspect of some embodiments of the present invention there is provided a method of identifying blood vessels in a thermal image of a section of a living body, the method comprising: convolving intensity data representing the thermal image with a predetermined vessel shapes filter thereby providing filtered data; calculating local derivatives of the filtered data along at least two dimensions, thereby providing derivative data; searching in the derivative data for local intensity extrema; and applying an interpolation procedure for generating contours between at least a few of the local intensity extrema, and identifying the contours as blood vessels.

According to some embodiments of the invention the method further comprises, prior to the convolution, inverting the intensity data by linear transformation.

According to some embodiments of the invention the method further comprises masking the intensity data so as to exclude at least a portion of the intensity data, the portion corresponding to picture-elements not belonging to blood vessels.

According to some embodiments of the invention the masking comprises calculating at least one of: local minimum, local maximum and local average for each picture-element of the thermal image.

According to some embodiments of the present invention the method further comprises normalizing the intensity data.

According to some embodiments of the present invention the calculation of the local derivatives comprises: calculating local derivatives along a first dimension; calculating local derivatives along a second dimension; and for each picture-element of the thermal image, selecting the highest of a respective derivative along the first direction and a respective derivative along the second direction.

According to some embodiments of the present invention the method further comprises, subsequently to the search for local intensity extrema, employing a noise reduction procedure for excluding isolated local intensity extrema.

According to some embodiments of the present invention the method further comprises generating a blood vessel map based on the identified blood vessels.

According to an aspect of some embodiments of the present invention there is provided a method of recognizing an individual based on a body section of the individual, comprising: identifying blood vessels in a thermal image of the body section, so as to generate a blood vessel map; searching a searchable database of blood vessel maps for a map entry which is similar to the blood vessel map; and identifying the individual based on the map entry.

According to an aspect of some embodiments of the present invention there is provided a method of estimating characteristic heat conduction of a section of a living body, comprising: obtaining a series of thermospatial representations describing the section of the living body while having at least two different shapes; for each shape, identifying at least one blood vessel in thermal data of a respective thermospatial representation and calculating a depth of the at least one blood vessel; determining thermal stabilization period for the at least one blood vessel; and determining the characteristic heat conduction based at least in part on the thermal stabilization period.

According to an aspect of some embodiments of the present invention there is provided apparatus for identifying blood vessels in a thermal image of a section of a living body, the apparatus comprising: a convolution unit, for convolving intensity data representing the thermal image with a predetermined vessel shapes filter thereby to provide filtered data; a derivative calculator, for calculating local derivatives of the filtered data along at least two dimensions, thereby providing derivative data; a local intensity extrema searcher, for searching in the derivative data for local intensity extrema; and an interpolator, for applying an interpolation procedure for generating contours between at least a few of the local intensity extrema, and identifying the contours as blood vessels.

According to some embodiments of the invention the apparatus further comprises an intensity data inverter for inverting the intensity data by linear transformation.

According to some embodiments of the invention the apparatus further comprising a masking unit for masking the intensity data so as to exclude at least a portion of the intensity data, the portion corresponding to picture-elements not belonging to blood vessels.

According to some embodiments of the invention the masking unit is operable to calculate at least one of: local minimum, local maximum and local average for each picture-element of the thermal image.

According to some embodiments of the present invention the apparatus further comprises a normalization unit for normalizing the intensity data.

According to some embodiments of the present invention the derivative calculator is operable to: calculate local derivatives along a first dimension; calculate local derivatives along a second dimension; and for each picture-element of the thermal image, select the highest of a respective derivative along the first direction and a respective derivative along the second direction.

According to some embodiments of the present invention the apparatus further comprises a noise reduction unit which employs a noise removal procedure to exclude isolated local intensity extrema.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1B:
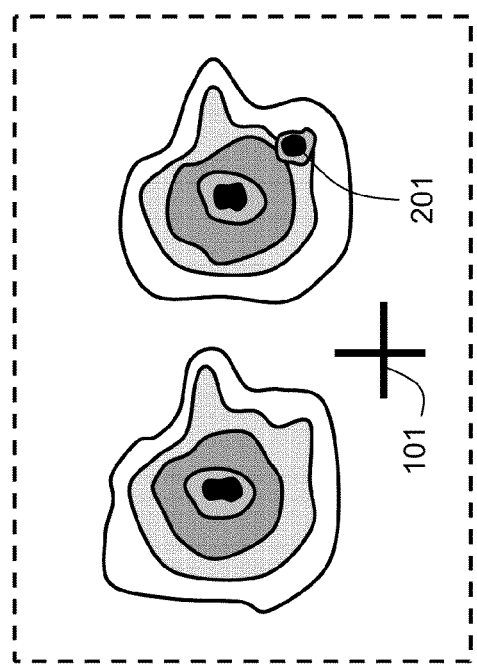
Figure 1A:
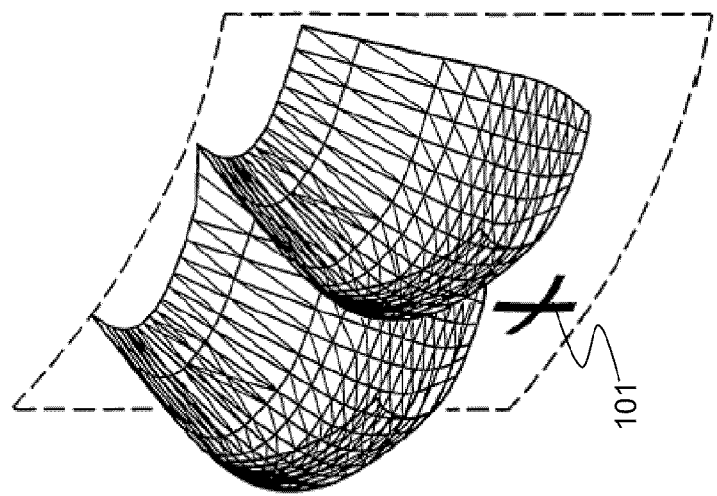
Figure 1C:
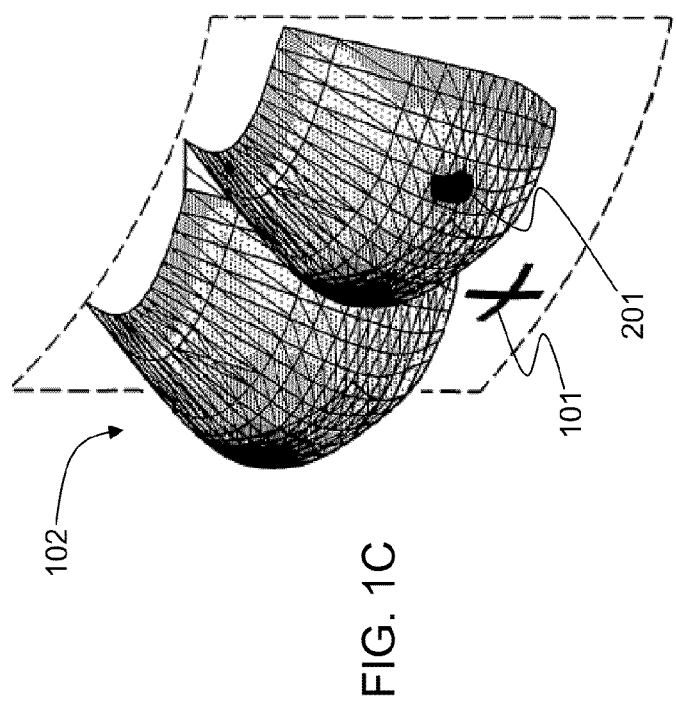
Figure 2:
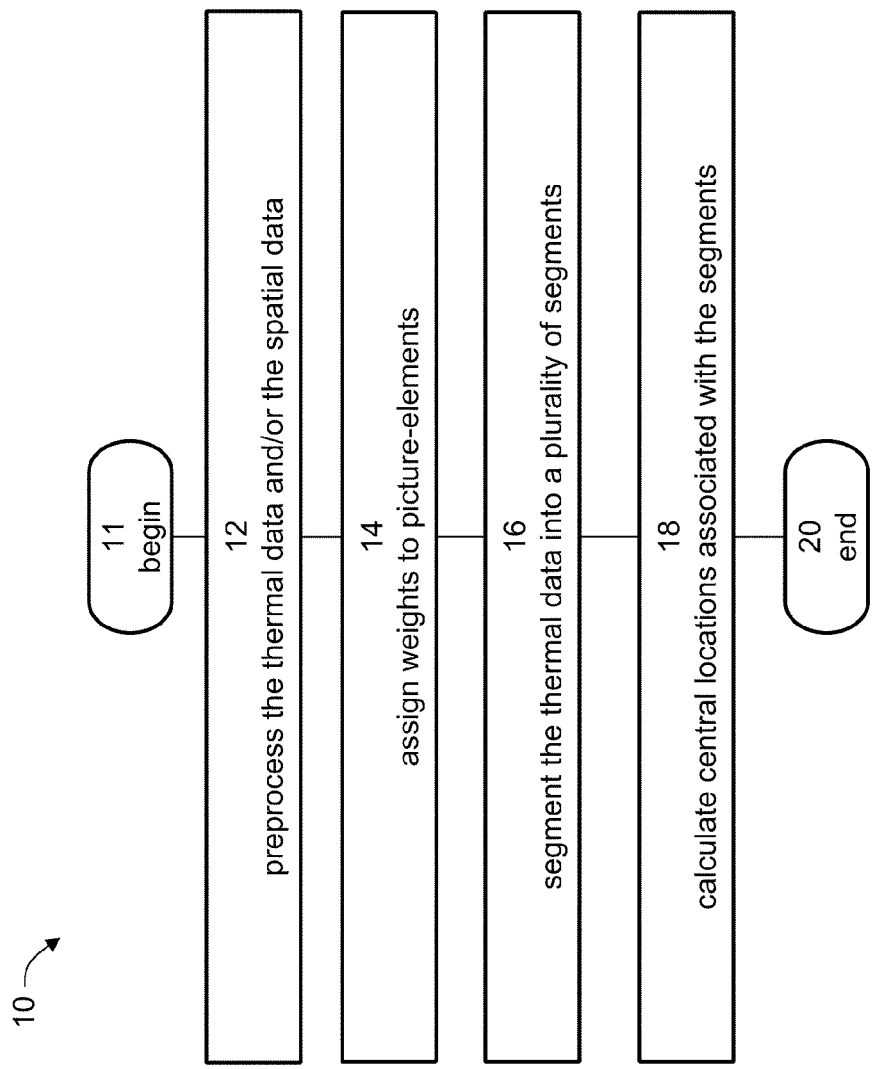
Figure 3A:
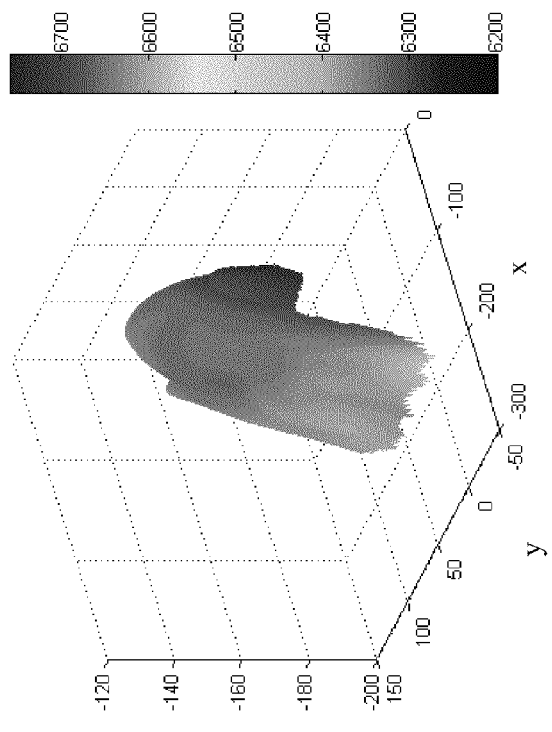
Figure 3B:
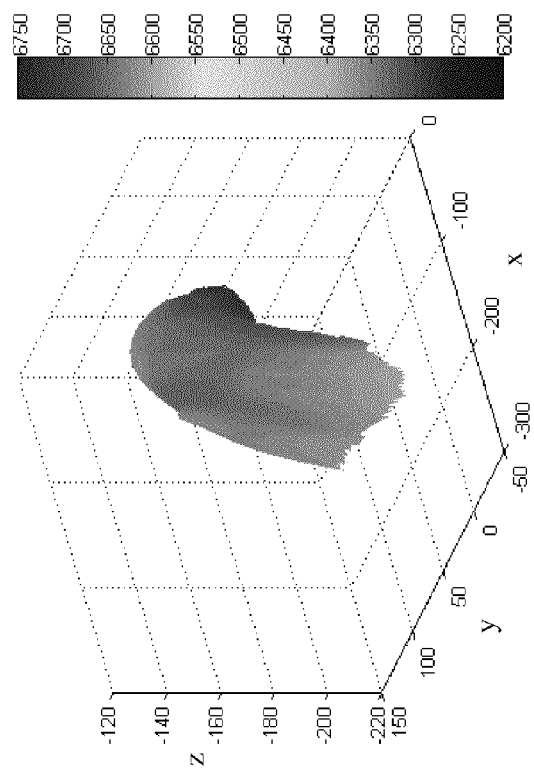
Figure 4A:
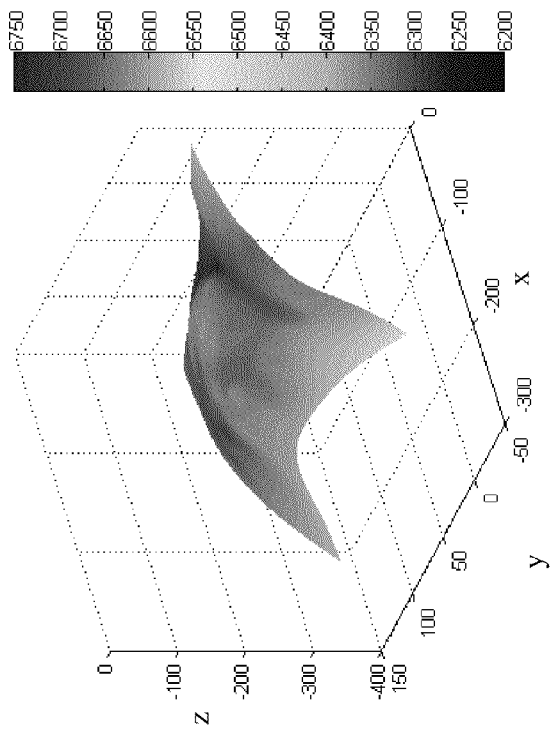
Figure 4B:
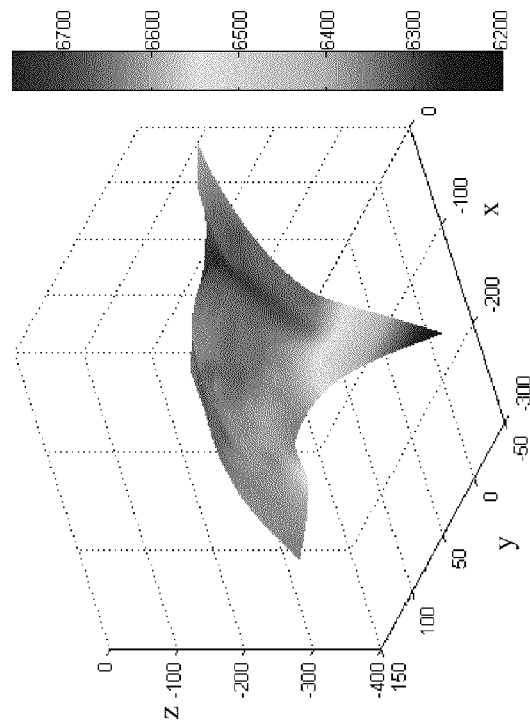
Figure 6:
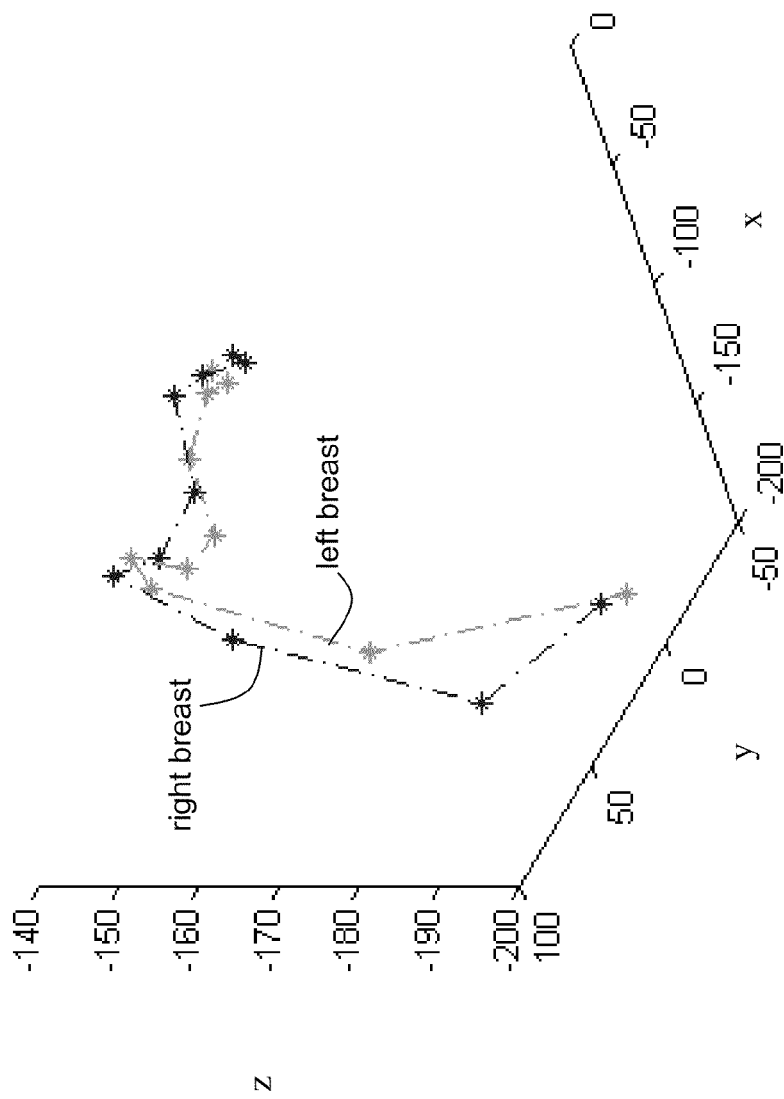
Figure 8A:
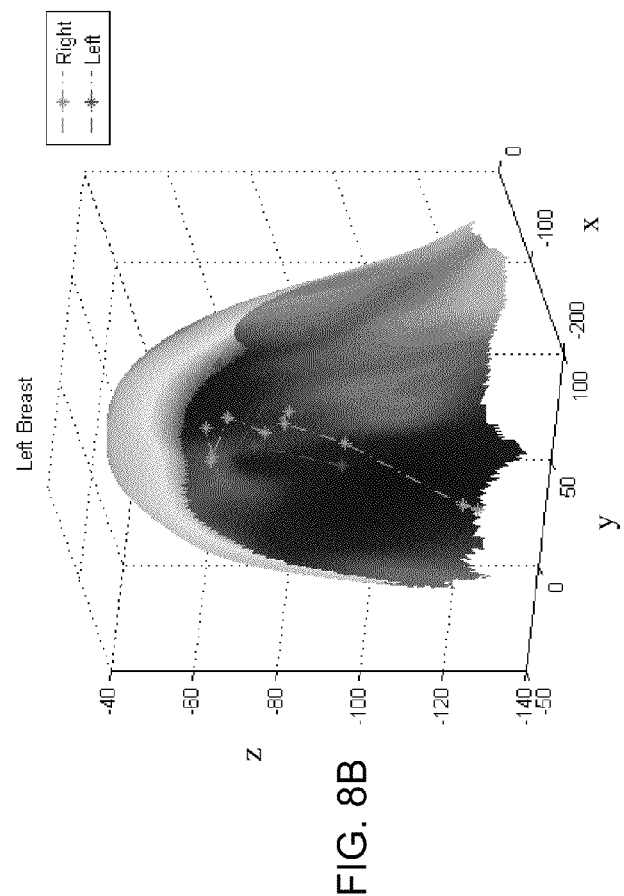
Figure 8B:
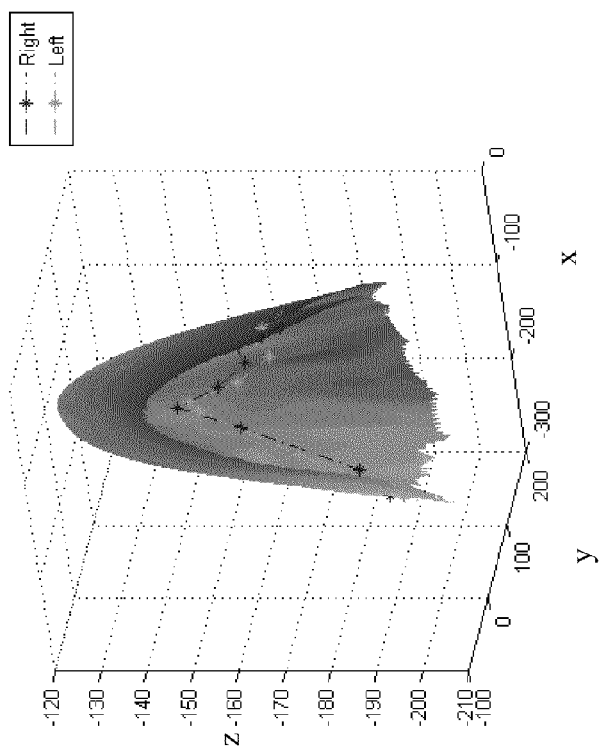
Figure 10:
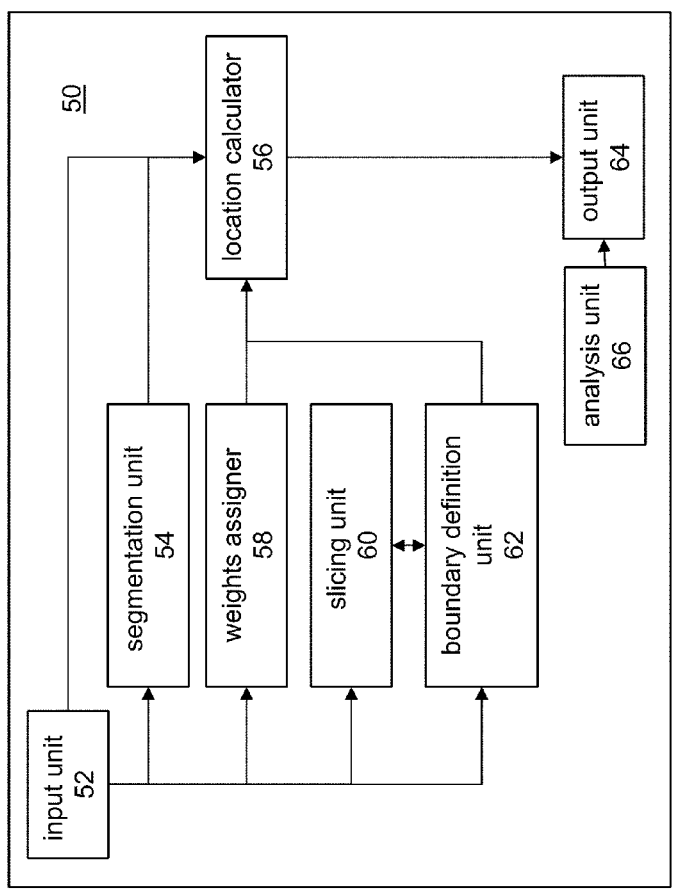
Figure 11:
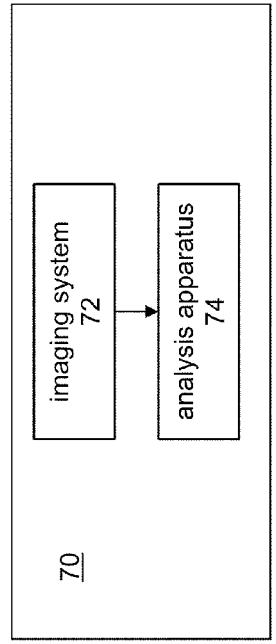
Figure 14:
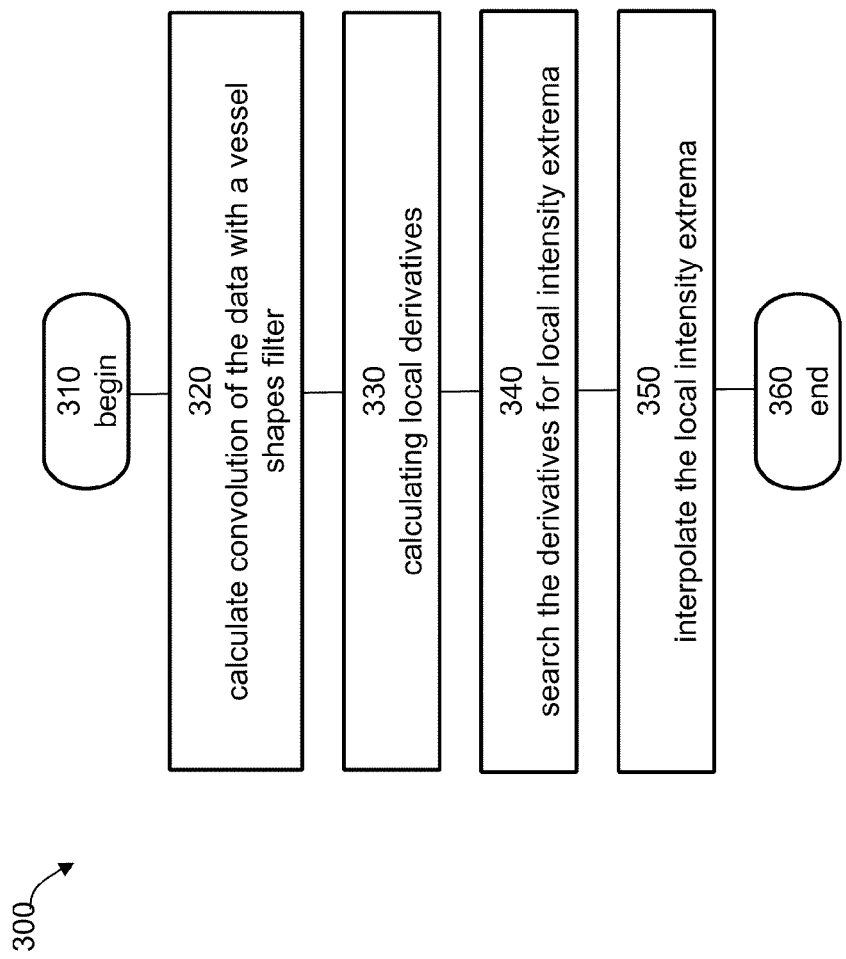
Figure 15:
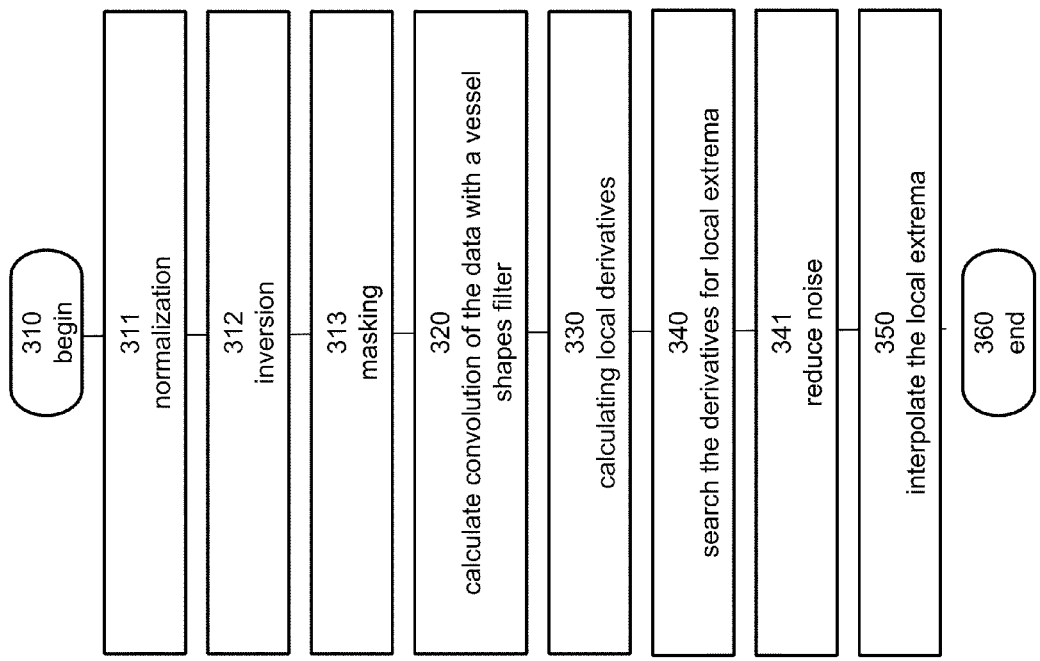
Figure 19:
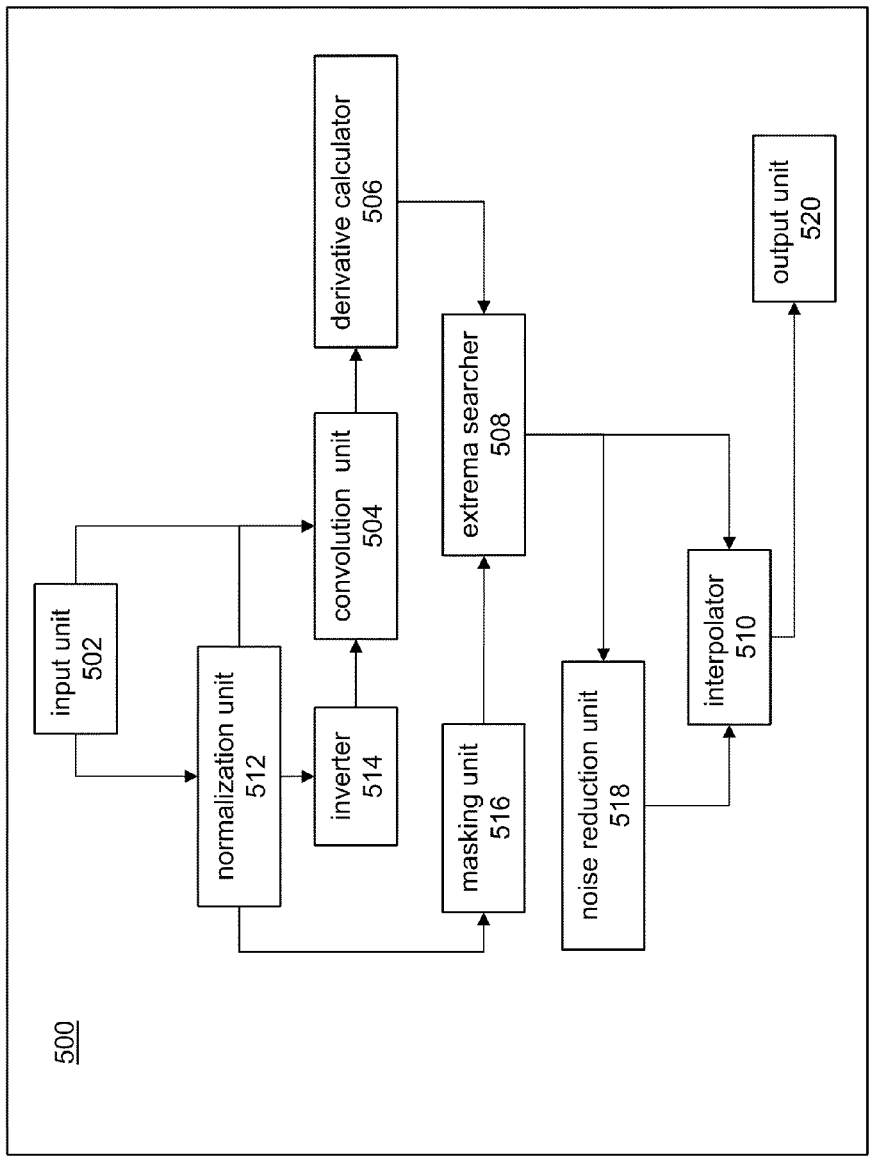
Figure 20:
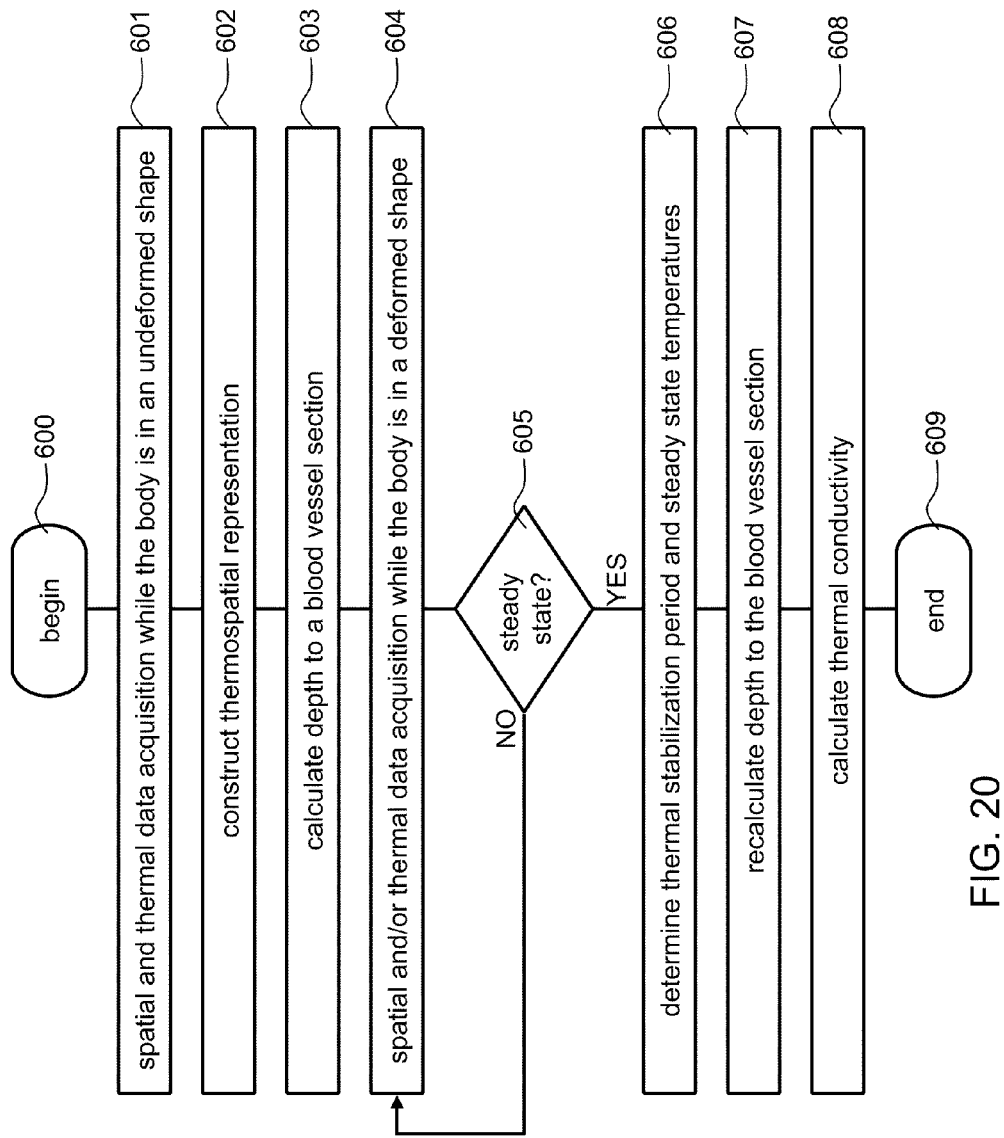
Figure 21A:
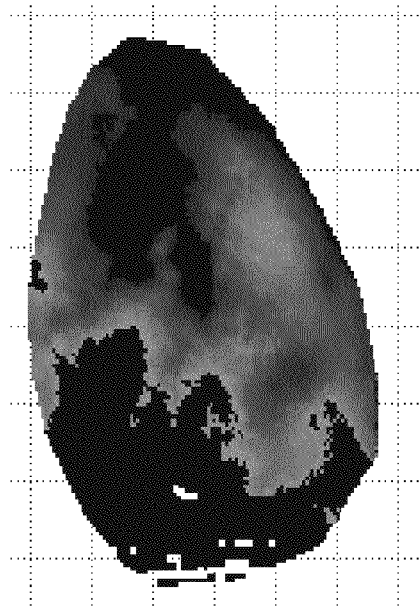
Figure 21B:
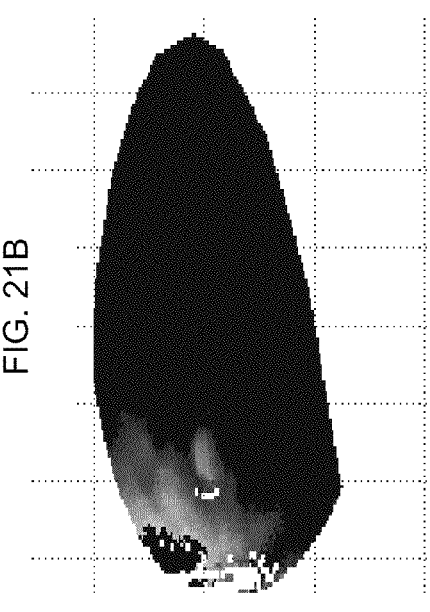
Figure 21C:
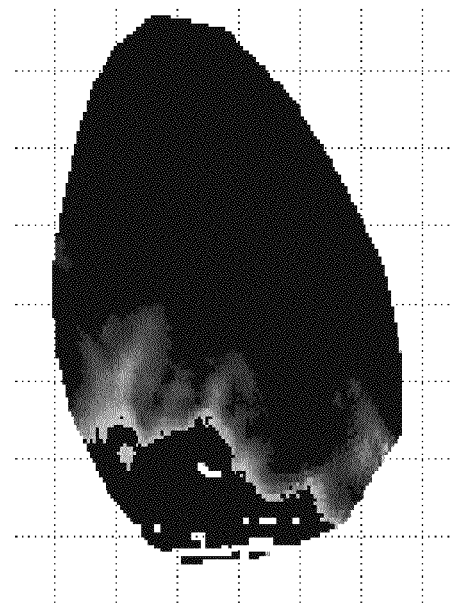
Figure 21D:
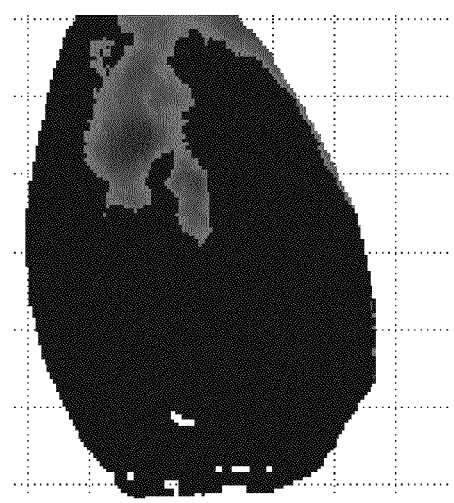
Figure 21F:
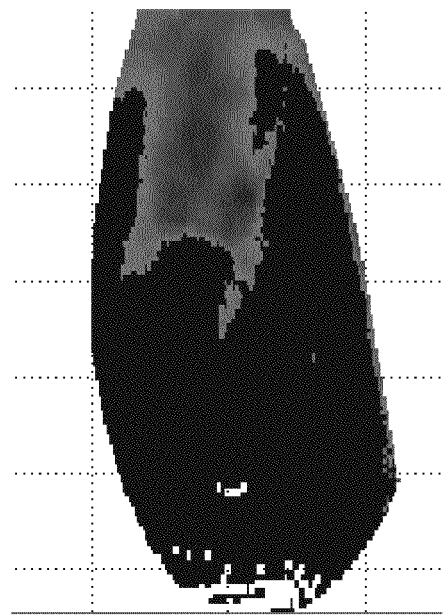
Figure 21E:
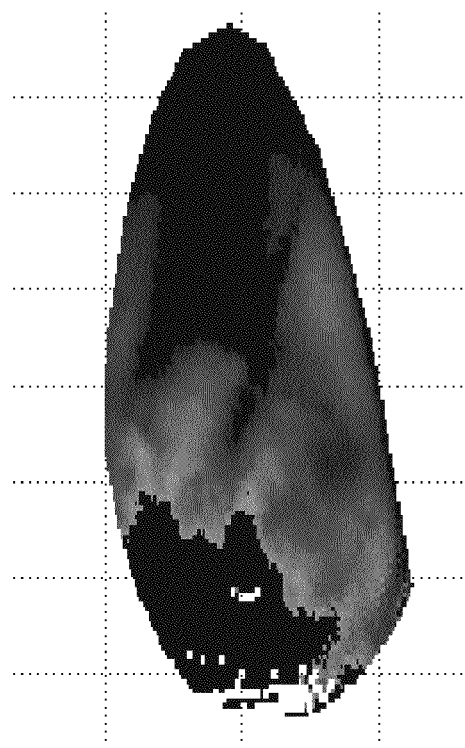

FIGS. 1A-C are schematic illustrations of a thermospatial representation, according to some embodiments of the present invention;

FIG. 2 is a flow chart diagram of a method suitable for determining a thermal signature of a body section, according to some embodiments of the present invention;

FIGS. 3A-B show boundaries definitions for a left breast (FIG. 3A) and a right breast (FIG. 3B), according to various exemplary embodiments of the present invention;

FIGS. 4A-B show a flip of a coordinate-system for a thermospatial representation of a left breast (FIG. 4A) and a non-flipped coordinate-system for a thermospatial representation of a right breast (FIG. 4B), according to various exemplary embodiments of the present invention;

FIGS. 5A-D illustrates sets of locations representing contours which can be used for determining a thermal signature, according to various exemplary embodiments of the present invention;

FIG. 6 shows a comparison between contours obtained according to some embodiments of the present invention for the left and right breasts illustrated in FIGS. 3A-B;

FIG. 7 is a flowchart diagram of a method suitable for determining presence or absence of a thermally distinguished region in a body section, according to various exemplary embodiments of the present invention;

FIGS. 8A-B show results of an exemplary implementation of the method illustrated in FIG. 7 for the case of breasts of women;

FIG. 9 is a flowchart diagram of an additional method suitable for determining presence or absence of a thermally distinguished region in a body section, according to some embodiments of the present invention;

FIG. 10 which is a schematic illustration of apparatus for determining a thermal signature of a body section, according to various exemplary embodiments of the present invention;

FIG. 11 which is a schematic illustration of an imaging and processing system, according to various exemplary embodiments of the present invention;

FIGS. 12A-F and 13A-E are schematic illustration of a thermospatial imaging system, according to various exemplary embodiments of the present invention;

FIGS. 14 and 15 are flowchart diagrams of a method suitable for identifying blood vessels in a thermal image of a section of a living body, according to various exemplary embodiments of the present invention;

FIGS. 16A-I and 17A-C are images obtained during the execution of various operations of the method illustrated in FIGS. 14 and 15;

FIG. 18 is a fragmentary schematic illustration of a rectangular grid of picture-elements;

FIG. 19 which is a schematic illustration of an apparatus for identifying blood vessels in a thermal image of a section of a living body, according to various exemplary embodiments of the present invention; and FIG. 20 is a flowchart diagram of a method suitable for estimating characteristic heat conduction, according to various exemplary embodiments of the present invention; and FIGS. 21A-F show representative segmentation operation, in accordance with some embodiments of the present invention.

DESCRIPTION OF SPECIFIC EMBODIMENTS
OF THE INVENTION

The present invention, in some embodiments thereof, relates to thermal images and, more particularly, but not exclusively, to the analysis of thermal images by determining a thermal signature within the images.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present inventors have devised an approach which enables the analysis of a thermal image, e.g., for the purpose determining a thermal signature of a body section. It was found by the present inventors that the thermal signature according to some embodiments of the present invention can be used to characterize the body section from the standpoint of its thermal properties and optimally to compare the body section to another body section and/or the same body section at an earlier time.

The thermal signature of the present embodiments can be based on a contour of locations over the thermal image the body section.

The thermal signature of the present embodiments can be based on a contour of locations within the body section. The contour of locations of the present invention can be planar or non-planar. In some embodiments of the present invention the thermal signature is a quantity which describes or characterizes the contour. This quantity can be the shape of the contour or a family of shapes to which the contour belongs. This quantity can also be a calculated quantity, such as a size or a density associated with the contour. This quantity can also describe similarity between the contour and a reference contour as further detailed hereinunder.

In some embodiments of the present invention, the thermal signature can be used for determining the likelihood for the presence of a thermally distinguishable region in the body section. When the thermal image is of a section of living body such as a breast of a male or female subject, the analysis of the present embodiments can be used to extract properties of the underlying tissue. For example, determination of the likelihood that a thermally distinguished region is present in the body section can be used for assessing whether or not the body section has a pathology such as a tumor or an inflammation.

An elevated temperature is generally associated with a tumor due to the metabolic abnormality of the tumor and proliferation of blood vessels (angiogenesis) at and/or near the tumor. In a cancerous tumor the cells proliferate faster and thus are more active and generate more heat. This tends to enhance the temperature differential between the tumor itself and the surrounding temperature. The present embodiments can therefore be used for diagnosis of cancer, particularly, but not exclusively breast cancer.

The surface information used for the analysis comprises thermal information and optionally also spatial information.

The thermal information comprises data pertaining to heat evacuated from or absorbed by the surface. Since different parts of the surface generally evacuate or absorb different amount of heat, the thermal information comprises a set of tuples, each comprising the coordinates of a region or a point on the surface and a thermal numerical value (e.g., temperature, thermal energy) associated with the point or region. The thermal information can be transformed to visible signals, in which case the thermal information is in the form of a thermographic image.

The thermal data is typically arranged gridwise in a plurality of picture-elements (e.g., pixels, arrangements of pixels)

representing the thermographic image. Each picture-element is represented by an intensity value or a grey-level over the grid. It is appreciated that the number of different intensity values can be different from the number of grey-levels. For example, an 8-bit display can generate 256 different grey-levels. However, in principle, the number of different intensity values corresponding to thermal information can be much larger. As a representative example, suppose that the thermal information spans over a range of 37° C. and is digitized with a resolution of 0.1° C. In this case, there are 370 different intensity values and the use of grey-levels is less accurate by a factor of approximately 1.4. Use of higher formats (e.g., 10 bit, 12 bit, 14 bit or higher) is also contemplated. For example, a photon thermal camera can provide information pertaining to the number of photons detected by the camera detector. Such information can extend over a range of about 6000-8000 intensity values.

In some embodiments of the present invention the processing of thermal data is performed using intensity values, and in some embodiments of the present invention the processing of thermal data is performed using grey-levels. Combinations of the two (such as double processing) are also contemplated.

The term "pixel" is sometimes abbreviated herein to indicate a picture-element. However, this is not intended to limit the meaning of the term "picture-element" which refers to a unit of the composition of an image.

The terms "thermographic image", "thermal image", "thermal information" and "thermal data" are used interchangeably throughout the specification without limiting the scope of the present invention in any way. Specifically, unless otherwise defined, the use of the term "thermographic image" is not to be considered as limited to the transformation of the thermal information into visible signals. For example, a thermographic image can be stored in the memory of a computer readable medium as a set of tuples as described above.

In embodiments in which the surface information also comprises spatial information, the spatial information comprises data pertaining to geometric properties of a surface which at least partially encloses a three-dimensional volume. In some embodiments of the present invention the surface is non-planar, e.g., curved. Generally, the surface is a two-dimensional object embedded in a three-dimensional space. Formally, a surface is a metric space induced by a smooth connected and compact Riemannian 2-manifold. Ideally, the geometric properties of the surface would be provided explicitly for example, the slope and curvature (or even other spatial derivatives or combinations thereof) for every point of the surface. Yet, such information is rarely attainable and the spatial information is provided for a sampled version of the surface, which is a set of points on the Riemannian 2-manifold and which is sufficient for describing the topology of the 2-manifold. Typically, the spatial information of the surface is a reduced version of a 3D spatial representation, which may be either a point-cloud or a 3D reconstruction (e.g., a polygonal mesh or a curvilinear mesh) based on the point cloud. The 3D spatial representation is expressed via a 3D coordinate-system, such as, but not limited to, Cartesian, Spherical, Ellipsoidal, 3D Parabolic or Paraboloidal coordinate 3D system.

The spatial data, in some embodiments of the present invention, can be in a form of an image. Since the spatial data represent the surface such image is typically a two-dimensional image which, in addition to indicating the lateral extent of body members, further indicates the relative or absolute distance of the body members, or portions thereof, from some reference point, such as the location of the imaging device. Thus, the image typically includes information residing on a surface of a three-dimensional body and not necessarily in the bulk. Yet, it is commonly acceptable to refer to such image as "a three-dimensional image" because the surface is conveniently defined over a three-dimensional system of coordinate. Thus, throughout this specification and in the claims section that follows, the terms "three-dimensional image" and "three-dimensional representation" primarily relate to surface entities.

The lateral dimensions of the spatial data are referred to as the x and y dimensions, and the range data (the depth or distance of the body members from a reference point) is referred to as the z dimension.

When the surface information of a body comprises thermal information and spatial information, it the surface information (thermal and spatial) of a body is typically in the form of a synthesized representation which includes both thermal data representing the thermal image and spatial data representing the surface, where the thermal data is associated with the spatial data (i.e., a tuple of the spatial data is associated with a heat-related value of the thermal data). Such representation is referred to as a thermospatial representation. The thermospatial representation can be in the form of digital data (e.g., a list of tuples associated with digital data describing thermal quantities) or in the form of an image (e.g., a three-dimensional image color-coded or grey-level coded according to the thermal data). A thermospatial representation in the form of an image is referred to hereinafter as a thermospatial image.

The thermospatial image is defined over a 3D spatial representation of the body and has thermal data associated with a surface of the 3D spatial representation, and arranged gridwise over the surface in a plurality of picture-elements (e.g., pixels, arrangements of pixels) each represented by an intensity value or a grey-level over the grid.

The term "voxel" is sometimes abbreviated herein to indicate a volume-element in the three-dimensional volume which is at least partially enclosed by the surface. However, this is not intended to limit the meaning of the term "volume-element" which refers to a unit of the composition of a volume.

When the thermospatial representation is in the form of digital data, the digital data describing thermal properties can also be expressed either in terms of intensities or in terms of grey-levels as described above. Digital thermospatial representation can also correspond to thermospatial image whereby each tuple corresponds to a picture-element of the image.

Typically, one or more thermographic images are mapped or projected onto the surface of the 3D spatial representation to form the thermospatial representation. The thermographic image to be projected onto the surface of the 3D spatial representation preferably comprises thermal data which are expressed over the same coordinate-system as the 3D spatial representation. Any type of thermal data can be used. In one embodiment the thermal data comprises absolute temperature values, in another embodiment the thermal data comprises relative temperature values each corresponding, e.g., to a temperature difference between a respective point of the surface and some reference point, in an additional embodiment, the thermal data comprises local temperature differences. Also contemplated, are combinations of the above types of temperature data, for example, the thermal data can comprise both absolute and relative temperature values, and the like.

Typically, but not obligatorily, the information in the thermographic image also includes the thermal conditions (e.g., temperature) at one or more reference markers.

The acquisition of surface data is typically performed by positioning the reference markers, e.g., by comparing their coordinates in the thermographic image with their coordinates in the 3D spatial representation, to thereby match, at least approximately, also other points hence to form the synthesized thermospatial representation.

The mapping of the thermographic image onto the surface of the 3D spatial representation is effected by a calibration procedure. Optionally and preferably, the mapping of thermographic images is accompanied by a correction procedure in which thermal emissivity considerations are employed.

The thermal emissivity of a body member is a dimensionless quantity defined as the ratio between the amount of thermal radiation emitted from the surface of the body member and the amount of thermal radiation emitted from a black body having the same temperature as the body member. Thus, the thermal emissivity of an idealized black body is 1 and the thermal emissivity of all other bodies is between 0 and 1. It is commonly assumed that the thermal emissivity of a body is generally equal to its thermal absorption factor.

The correction procedure can be performed using estimated thermal characteristics of the body of interest. Specifically, the thermographic image is mapped onto a non-planar surface describing the body taking into account differences in the emissivity of regions on the surface of the body. A region with a different emissivity value compared to its surrounding, can be, for example, a scarred region, a pigmented region, a nipple region on the breast, a nevus. Additionally, the emissivity values of subjects with different skin colors may differ.

The correction procedure may also employ a heat distribution function describing the distribution of heat away from a heat source located in of on the surface the body section. A heat distribution function provides the heat as a function of the distance and angle relative to the heat source.

In some embodiments of the present invention, the thermographic image is weighted according to the different emissivity values of the surface. For example, when information acquired by a thermal imaging device include temperature or energy values, at least a portion of the temperature or energy values can be divided by the emissivity values of the respective regions on the surface of the body. One of ordinary skill in the art will appreciate that such procedure results in effective temperature or energy values which are higher than the values acquired by the thermal imaging device. Since different regions may be characterized by different emissivity values, the weighted thermographic image provides better estimate regarding the heat emitted from the surface of the body.

A representative example of a synthesized thermospatial image for the case that the body comprise the breasts of a female or male subject is illustrated in FIGS. 1A-C, showing a 3D spatial representation illustrated as a non-planar surface (FIG. 1A), a thermographic image illustrated as planar isothermal contours (FIG. 1B), and a synthesized thermospatial image formed by mapping the thermographic image on a surface of the 3D spatial representation (FIG. 1C). As illustrated, the thermal data of the thermospatial image is represented as grey-level values over a grid generally shown at 102. It is to be understood that the representation according to grey-level values is for illustrative purposes and is not to be considered as limiting. As explained above, the processing of thermal data can also be performed using intensity values. Also shown in FIGS. 1A-C, is a reference marker 101 which optionally, but not obligatorily, can be used for the mapping.

In some embodiments of the present invention a series of thermal images of a section of a living body is obtained. Different thermal images of the series include thermal data acquired from the body section at different time instants. Such series of thermal images can be used by the present embodiments to determine thermal changes occurred in the body section over time.

In some embodiments of the present invention a series of thermospatial representation of a section of a living body is obtained. Different thermospatial representations of the series include thermal data acquired from the body section at different time instants. Such series of thermospatial representations can be used by the present embodiments to determine thermal and optionally spatial changes occurred in the body section over time.

The series can include any number of thermal images or thermospatial representations. It was found by the inventors of the present invention that two thermal images or thermospatial representations are sufficient to perform the analysis, but more than two thermal images or thermospatial representations (e.g., 3, 4, 5 or more) can also be used, for example, to increase accuracy of the results and/or to allow selection of best acquisitions.

The 3D spatial representation, thermographic image and synthesized thermospatial image can be obtained in any technique known in the art, such as the technique disclosed in International Patent Publication No. WO 2006/003658, U.S. Published Application No. 20010046316, and U.S. Pat. Nos. 6,442,419, 6,765,607, 6,965,690, 6,701,081, 6,801,257, 6,201,541, 6,167,151, 6,167,151, 6,094,198 and 7,292,719.

Some embodiments of the invention can be embodied on a tangible medium such as a computer for performing the method steps. Some embodiments of the invention can be embodied on a computer readable medium, comprising computer readable instructions for carrying out the method steps. Some embodiments of the invention can also be embodied in electronic device having digital computer capabilities arranged to run the computer program on the tangible medium or execute the instruction on a computer readable medium. Computer programs implementing method steps of the present embodiments can commonly be distributed to users on a tangible distribution medium. From the distribution medium, the computer programs can be copied to a hard disk or a similar intermediate storage medium. The computer programs can be run by loading the computer instructions either from their distribution medium or their intermediate storage medium into the execution memory of the computer, configuring the computer to act in accordance with the method of this invention. All these operations are well-known to those skilled in the art of computer systems.

FIG. 2 is a flow chart diagram of a method 10 suitable for determining a thermal signature of a body section, according to some embodiments of the present invention. The body section can be one or more organs, e.g., a breast or a pair of breasts, or a part of an organ, e.g., a part of a breast. In some embodiments of the present invention, the thermal signature is determined by processing thermal data acquired from the surface of the body section. In some embodiments of the present invention, the thermal signature is determined by processing thermospatial representation of the body section.

It is to be understood that, unless otherwise defined, the operations of the method described hereinbelow can be executed either contemporaneously or sequentially in many combinations or orders of execution. Specifically, the ordering of the flowchart diagrams is not to be considered as limiting. For example, two or more operations, appearing in the following description or in the flowchart diagrams in a particular order, can be executed in a different order (e.g., a reverse order) or substantially contemporaneously. Additionally, several operations method steps described below are optional and may not be executed.

The method begins at 11 and optionally continues to 12 at which the spatial and/or thermal data is preprocessed. In some embodiments of the present invention the preprocessing operation includes definition of one or more spatial boundaries for the surface, so as to define a region-of-interest for the analysis. This embodiment is particularly useful when the thermal signature is determined from a thermospatial representation of the body section. For example, when the body section is a section of a living body and spatial data of the thermospatial representation comprises data representing a surface of tissue being nearby to the body section, the method preprocessing operation can include defining a spatial boundary between the surface of the body section and surface of the nearby tissue. In this embodiment, the surface of the nearby tissue is preferably excluded from the analysis. FIGS. 3A-B exemplify boundaries definitions for the cases in which the body section is a left breast (FIG. 3A) and a right breast (FIG. 3B).

In some embodiments of the present invention the preprocessing comprises transformation of coordinates. For example, when the method is executed for determining the thermal signature of more than one body sections having similar shapes, the method preferably transform the coordinates of one or more body section so as to ensure that all body sections are described by the same coordinate-system. For example, when the method determines the thermal signature of a left breast and a right breast, the system of coordinates of the thermal image and/or thermospatial representation of one of the breasts can be flipped so as to describe both thermal images and both thermospatial representations using the same coordinate-system. FIGS. 4A-B exemplify a flip of a coordinate-system for a thermospatial representation of a left breast (FIG. 4A) and a non-flipped coordinate-system for a thermospatial representation of a right breast (FIG. 4B).

In some embodiments of the present invention the preprocessing comprises normalization of the thermal data. The normalization is useful when it is desired not to work with too high values of intensities. In various exemplary embodiments of the invention the normalization is performed so as to transform the range of thermal values within the thermal data to a predetermined range between a predetermined minimal thermal value and a predetermined maximal thermal value. This can be done using a linear transformation as known in the art. A typical value for the predetermined minimal thermal value is 1, and a typical value for the predetermined maximal thermal value is 10. Other ranges or normalization schemes are not excluded from the scope of the present invention.

In some embodiments of the present invention the preprocessing operation includes slicing of the surface described by the spatial data to a plurality of slices. In these embodiments, the thermal signature can be determined separately for each slice. The slicing can be along a normal direction (away from the body), parallel direction or azimuthal direction as desired. The slicing can also be according to anatomical information (for example a different slice for a nipple region). Also contemplated is arbitrary slicing, in which case the surface is sliced to N regions.

In some embodiments of the present invention the preprocessing comprises normalization of the spatial data. The normalization is useful when it is desired to compare between thermal signatures of different body sections, for example, body sections having similar shapes but different sizes. These embodiments are particularly useful when the body section is a breast and it is desired to compare the thermal signature of breasts of different sizes (e.g., a left breast to a right breast of the same subject, or a breast of one subject to a breast of another subject).

In some embodiments of the present invention the method continues to 14 at which the method assigns weights for at least some of the picture-elements. The weights can be calculated based on Z dimension. Since the thermal and spatial data includes surface information, the weights are assigned to picture-elements which reside on the surface of the body section.

In various exemplary embodiments of the invention the weights are assigned by calculating spatial derivatives. For example, the method can calculate a height gradient for the picture-elements with respect to one or more lateral directions. Consider, for example, a picture-element p which belongs to a thermospatial representation and which is located at location (x, y, z), where x and y are the two lateral coordinates and z is a height coordinate. In the present embodiments, the method can calculate at least one of the derivatives $G_x=dz/dx$ and/or $G_y=dz/dy$. This can be done using any known image processing procedure, such as, but not limited to, the by application of the Sobel operator which is known in the art and described, e.g., in Sobel, I., Feldman, G., "A 3×3 Isotropic Gradient Operator for Image Processing", presented at a talk at the Stanford Artificial Project in 1968, unpublished but often cited, orig. in Pattern Classification and Scene Analysis, Duda, R. and Hart, P., John Wiley and Sons, '73, pp271-2). The weight $w_p$ of picture-element p can be calculated using the calculated derivatives. For example, when $G_x$ is calculated, $w_p$ can be set to $G_x$, $|G_x|$, $1+|G_x|$, $\sqrt{1+G_x^2}$, etc.; when $G_y$ is calculated, $w_p$ can be set to $G_y$, $|G_y|$, $1+|G_y|$, $\sqrt{1+G_y^2}$, etc.; and when both $G_x$ and $G_y$ are calculated $w_p$ can be set to $1+|G_x|+|G_y|$, $\sqrt{1+G_x^2+G_y^2}$, etc.

The procedure can be repeated for at least some of the picture-elements in the thermospatial representation, more preferably for all the picture-elements under analysis. It is appreciated that in the above example $w_p>1$ for all values of $G_x$ and $G_y$. Thus, in the present embodiment the picture-elements are assigned with weights which are greater than unity.

At 16 the method segments the thermal data. In embodiments in which the method processes a thermal image, the segmentation is applied to the thermal data which represent the thermal image. In embodiments in which the method processes a thermospatial representation, the segmentation is applied to the thermal data which forms, together with the spatial data, the thermospatial representation.

The result of the segmentation operation is a plurality of segments, each defined as a range of thermal values (intensities, grey levels or normalized values in embodiments in which the normalization is employed).

The segments are preferably mutually exclusives, namely that there is no overlap between segments. Each thermal value over the thermal data preferably belongs to one segment. Since the thermospatial representation includes spatial data associated with the thermal data, each picture-element of the thermospatial representation is also associated with one of the segments. Specifically, all picture-elements having thermal values which are within a range of thermal values defining a particular segment are said to be associated with that segment. Formally, denoting the ith segment by $s_i$ and the range of thermal values which defines $s_i$ by $R_i$, the set $P_i$ of picture-elements which are associated with $s_i$ includes all picture-elements which have a thermal value g satisfying $g \in R_i$.

It is noted that the segmentation is of the thermal data and not the spatial data, although both type of data belong to the same thermospatial representation. Therefore, picture-elements which are associated with a segment do not necessarily reside on the same region of the surface. On the other hand, the thermal data of all picture-elements associated with a segment are within the same range. FIGS. 21A-F show representative segmentation operation, in accordance with some embodiments of the present invention. A different segment is shown in each of FIGS. 21A-F. As shown, picture-elements which are associated with a segment may or may not reside on the same region of the surface.

The number of segments can be predetermined or it can be determined by the method. The segmentation can be done according to the range of values within the thermal data or within the portion of the thermal data under investigation or within the normalized thermal data. The segmentation can be uniform across the range of intensities. For example, when there are M different thermal values and N segments, each segment is defined over a range of approximately M/N thermal values. Without loss of generality, the thermal values can be integers from 1 to N. Denoting the N segments by $s_1$, $s_2, \ldots, s_N$, the first segment $s_1$ can include thermal data values from 1 to approximately M/N, the second segment $s_2$ can include thermal data values from approximately M/N+1 to approximately 2M/N, etc. The special case in which N=M (i.e., each segment is defined by a single thermal value) is not excluded from the scope of the present invention. Thus, the term "range of thermal values" as used herein also encompasses the case in which the range includes a single thermal value.

The segmentation can also be non-uniform, in which case the range of values for some segments is wider than the others. This embodiment is useful when the uniform segmentation results in some segments which are associated with a small number of picture-elements.

At 18 the method calculates a set of locations, which is subsequently used for determining the thermal signature of the body section. In embodiments in which the method processes a thermal image, each of the locations in the set can represent a picture-element of the thermal image. In embodiments in which the method processes a thermospatial representation each location can represent a surface-element (e.g., a pixel) or a volume-element (e.g., a voxel) of the thermospatial representation. For a given segment $s_i$ ($1 \leq i \leq N$) the method uses the spatial coordinates of the picture-elements associated with $s_i$ (the picture-elements in set $P_i$) to calculate a spatial location $L_i$ which is central with respect to the locations of the picture-elements in $P_i$.

The location $L_i$ can be calculated using any technique known in the art. Typically, the calculation involves some type of averaging procedure, including, without limitation, arithmetic average, geometric average, harmonic average, root-mean-square, generalized (arbitrary power) root-mean-power and the like. When the picture-elements in the thermal image, thermospatial representation or portion thereof are assigned with weights (see 14 in FIG. 2) the method preferably calculates $L_i$ as a weighted average of the locations of the picture-element in the set $P_i$. A weighted average can be viewed as a type of "center-of-mass" calculation whereby the weights of the picture-elements in $P_i$ play the role of the "masses" of those picture-elements. This description is particularly understood in embodiments in which the weights are correlated with the areas of the picture-elements, because larger picture-elements can be considered as objects of larger "masses". The calculation the central locations can be repeated for several segments, more preferably for all segments, so as to provide a set of locations, each being central with respect to the picture-element associated with one of the segments. The set of locations represents a contour in a two-dimensional or a three-dimensional space. The contour can be planar or non-planar, branched or non-branched, continuous or discontinuous.

Figure 5A:
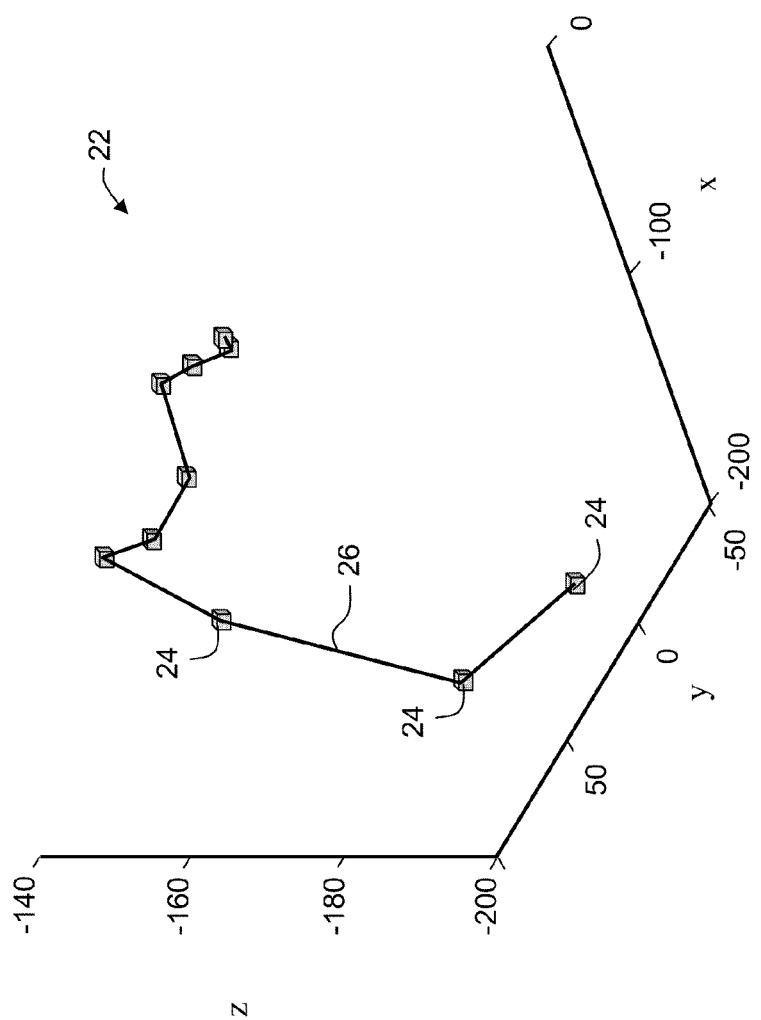
Figure 5B:
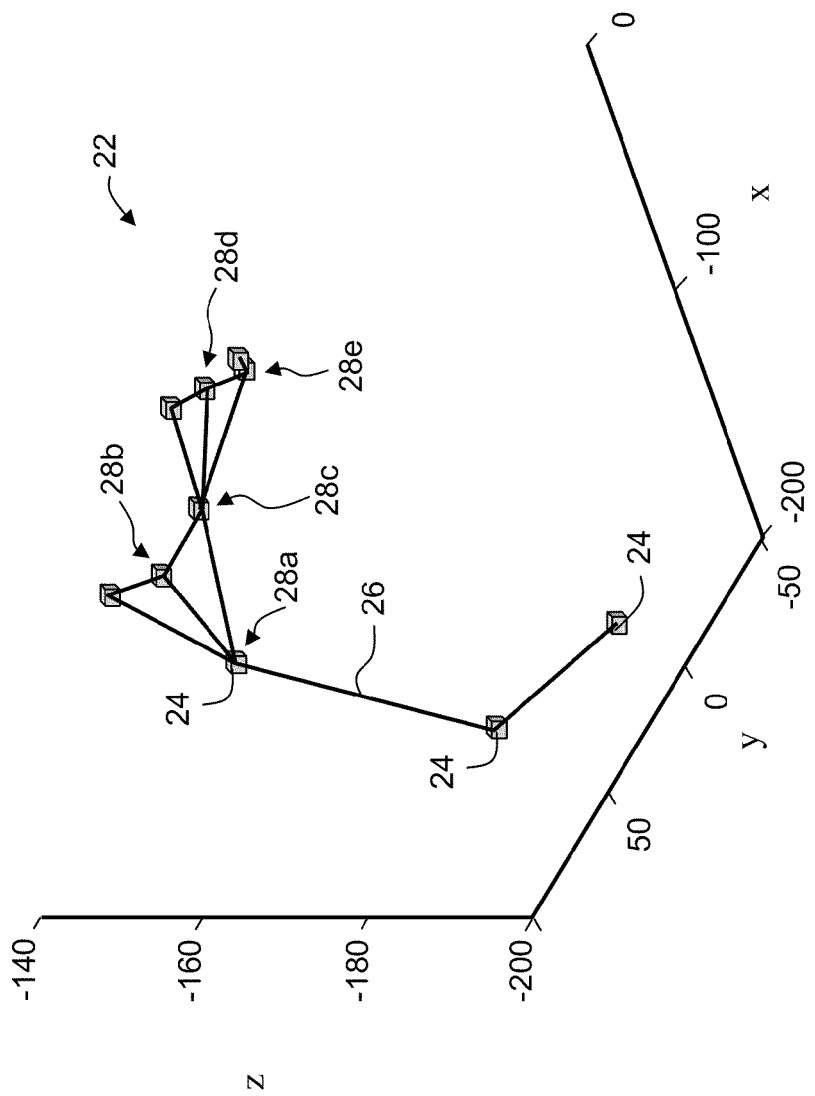
Figure 5D:
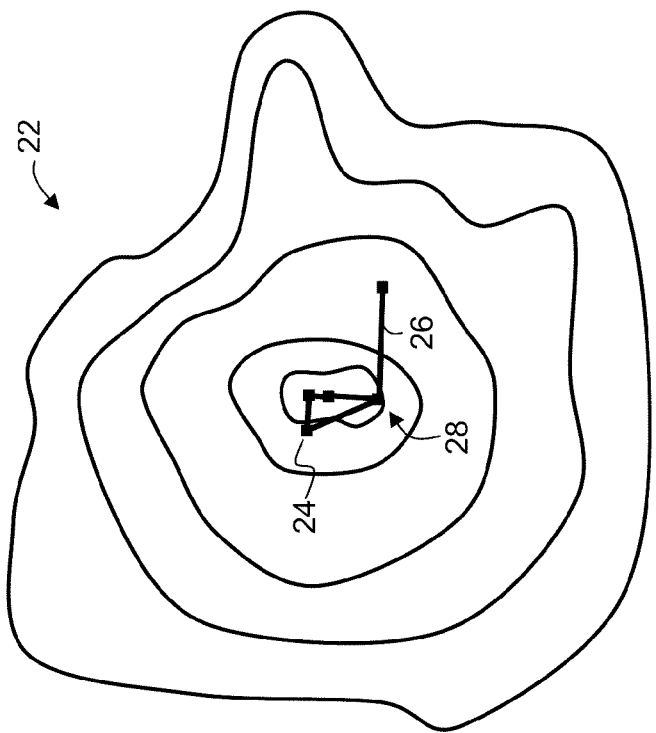
Figure 5C:
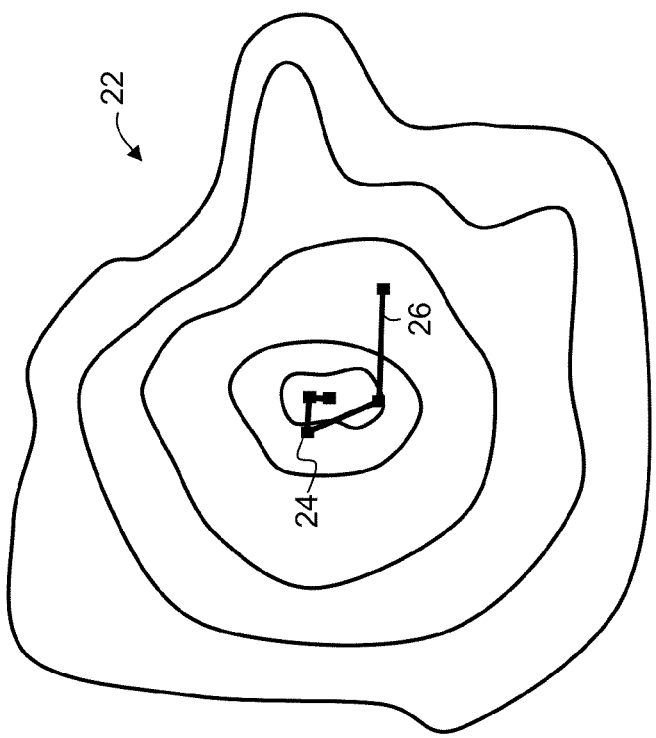

FIG. 5A shows a set 22 of locations 24 (10 locations are shown) which represents a contour 26, in an embodiment in which the contour is a one-dimensional non-planar object embedded in a three-dimensional space. Although the contour is shown in FIG. 5A as a non-branched set of lines connecting the locations, this need not necessarily be the case, since in some embodiments of the present invention the contour can have one or more branches. FIG. 5B shows contour 26 in an embodiment in which contour 26 is branched. In the representative example of FIG. 5B, contour 26 includes fives branches, generally shown at 28a, 28b, 28c, 28d, and 28e, where each branch is at one of the locations. FIGS. 5C-D show contour 26 in embodiments in which the contour is a one-dimensional planar object embedded in a two-dimensional space. In FIG. 5C contour 26 is non-branched, and in FIG. 5D contour 26 is branched. In the representative example of FIG. 5D, contour 26 includes one branch, generally shown at 28.

While the lines connecting the locations are shown as straight lines in FIGS. 5A-D this need not necessarily be the case, since, for some applications, it may be desired to form the contour using a fitting procedure (e.g., a polynomial fit) in which case the lines can be curved.

In some embodiments of the present invention the contour is obtained in accordance of the order of the thermal value ranges from which they were calculated. Specifically, the first point of the contour correspond to a segment defined by the lowest range of thermal values, the second point of the contour correspond to a segment defined by the next to lowest range and so on. For example, consider a case in which there are N thermal values 1, 2, . . . , N, and N segments $s_1$, $s_2, \ldots, s_N$, whereby $s_1$ is defined by the (single) thermal value 1, $s_2$ is defined by the thermal value 2, and so on. In this case, the first point of the contour corresponds to $s_1$, the second point of the contour corresponds to $s_2$, and so on. Consider another example in which there are 3N thermal values 1, 2, . . . , 3N and N segments $s_1, s_2, \ldots, s_N$, whereby $s_1$ is defined by the range [1,3], $s_2$ is defined by the range [4,6] and so on. In this case, the first point of the contour corresponds to $s_1$, the second point of the contour corresponds to $s_2$, and so on.

The thermal signature of the present embodiments is based on contour 26. In some embodiments of the present invention the thermal signature is a quantity which describes or characterizes the contour. This quantity can be the specific shape of the contour and/or a family of shapes (e.g., planar/non-planar, closed/open, self intersecting/non-self intersecting, branched/non-branched) to which the contour belongs.

The thermal signature can also be a calculated quantity, such as a size associated with the contour. For example, the thermal signature can be the total length of the contour, the maximal or mean distance between two points on the curve, and the like.

The thermal signature can also be a density associated with the contour. For example, a density can be defined as the number of picture-element, surface-elements and/or volume-elements which define the contour divided by the total length of the contour.

The thermal signature can also be a vector which describes the Euclidean distance between the locations of successive picture-element, surface-elements and/or volume-elements which define the contour. A representative example of such vector is $(L_1L_2, L_2L_3, \ldots, L_{N-1}L_N)$ where $L_iL_{i+1}$ (i=1, . . . , N−1) is the Euclidean distance between location $L_i$ and location $L_{i+1}$. This embodiment is particularly useful in embodiments in which it is desired to compare two thermal signatures, as further detailed hereinbelow.

The method can also compare the thermal signature to a reference thermal signature. The reference thermal signature generally corresponds to a reference thermospatial representation, which can be obtained from a library or can be constructed by the method of the present embodiments.

The reference thermospatial representation can describe a reference body section other than the body section being analyzed. For example, the reference body section can be a body section which is similar in shape to the body section being analyzed. When the body section is a breast, the reference body section can be the other breast of the same subject. In this embodiment, the aforementioned transformation of coordinates is preferably employed so as to facilitate conceptual overlap of one body section over the other.

In some embodiments of the present invention the reference thermospatial representation includes history data of the body section. Thus, the reference body section can be the same body section as captured at an earlier time. The inclusion of history data in the thermospatial representation can be achieved by recording the reference thermospatial representation and/or the thermal signature at a date earlier than the date at which the method is executed. This embodiment can also be useful for monitoring changes in the body section over time.

When a series of thermospatial representations is obtained, the reference thermospatial representation can be one of the thermospatial representations of the series. In some embodiments of the present invention the ambient temperature at the surface of the body section is changed between two successive captures of surface information, and the corresponding thermospatial representations are obtained. In these embodiments, the thermal signatures of two such successive thermospatial representations are determined and compared. Thus, in these embodiments, the reference thermal signature is the thermal signature which corresponds to the state of the body section prior to the change in ambient temperature.

A change in the ambient temperature corresponds to different boundary conditions for different thermospatial representations. Specifically, in these embodiments, two successive thermospatial representations describe the body section while the subject is exposed to two different ambient temperatures. A change in the ambient temperature can be imposed, for example, by establishing contact between a cold object and the body section or directing a flow of cold gas (e.g., air) to the surface of the body section between successive data acquisitions. Also contemplated is a procedure in which the body section is immersed in cold liquid (e.g., water) between successive data acquisitions. Also contemplated is a procedure in which another body section is exposed to a different (e.g., lower) temperature so as to ensure transient thermal condition. For example, the subject can immerse his or her limb in a cold liquid (e.g., water).

In some embodiments of the present invention the reference thermospatial representation is obtained by means of biomedical engineering.

The comparison between the thermal signatures is typically according to the way the thermal signature is determined based on the contour.

When the thermal signature is defined as the shape of the contour the comparison is preferably done shape-wise. In this embodiment, the contour and the reference contour are preferably defined in the same coordinate-system. FIG. 6 shows a comparison between contours obtained for the left and right breasts illustrated in FIGS. 3A-B.

In various exemplary embodiments of the invention a contour or curve alignment procedure is employed for the comparison of the contour and the reference contour. For example, the method can perform a pairwise calculation of the distances between the locations defining the contour and the locations defining the reference contour, to provide a vector of distances. A representative example of such vector is $(L_1L'_1, L_2L'_2, \ldots, L_NL'_N)$ where $L_iL'_i$ ($i=1, \ldots, N$) is the Euclidean distance between location $L_i$ in the contour and location $L'_i$ in the reference contour. A vector of distances can also be obtained when the vectors are of different lengths. In this case a dilution procedure for one or both contour preferably precedes the calculation of distances.

Once a vector of distances is obtained the method can use the vector to calculate a score which characterizes the similarity or dissimilarity between the thermal signatures. The score can include, for example, norm, mean and/or variance of the vector. The score can also include a combination between these quantities. In various exemplary embodiments of the invention the score is the sum of squares of the mean and standard deviation of the vector.

Once a vector of distances is obtained the method can calculate the norm of this vector so as to quantify the similarity or dissimilarity between the thermal signatures using a single score. It was found by the present inventors that the similarity or dissimilarity between the thermal signatures can be used to distinguish between different types of tumors (e.g., whether or not the thermally distinguished region is a tumor, or whether the tumor is malignant or benign).

Other contour or curve alignment procedures are not excluded from the scope of the present invention. Representative examples of other procedures include, without limitation, the procedures disclosed in Gareth M. James, Annals of Applied Statistics (2007) Vol. 1, No. 2 480-501; and Peter J. Green and Kanti Mardia (2005), arXiv:math/0503712.

When the thermal signature is defined as a calculated quantity, such size density and the like, the comparison between the thermal signature is based on the calculated quantity, wherein large deviations between the respective calculated quantities correspond to high level of dissimilarity between the thermal signatures and vice versa.

In some embodiments of the present invention the method compares the morphology associated with one or more segments with the morphology associated with the respective segments in the reference representation. Such comparison is optionally used by the method to determine similarity or dissimilarity between the two representations. For example, if the reference representation corresponds to a healthy body section and a high degree of similarity was found between the morphologies associated with respective segments, the method can determine that it is likely that the body section under investigation is also healthy. On the other hand is a high degree of dissimilarity was found between the morphologies associated with respective segments, the method can determine that it is likely that the body section under investigation has a thermally distinguished region.

The method ends at 20.

Reference is now made to FIG. 7 which is a flowchart diagram of a method 30 suitable for determining presence or absence of a thermally distinguished region in a body section, according to various exemplary embodiments of the present invention.

The method begins at 31 and continues to 32 at which the method determines a thermal signature in the body section, for example, using selected operations of method 10. At 33 the method compares the thermal signature with a reference thermal signature of a reference thermospatial representation as further detailed hereinabove. Preferably, the reference body section is devoid of thermally distinguishable region.

The method continues to decision 34 at which the method determine whether or not the thermal signature is similar to the reference thermal signature. The similarity can be determined according to any of the criteria described above. In various exemplary embodiments of the invention the similarity is quantified by a score as further detailed hereinabove.

If the signatures are similar, the method continues to 35 at which the method determines that a thermally distinguished region is not likely to be present in the body section. If the signatures are dissimilar, the method continues to 36 at which the method determines that a thermally distinguished region is likely to be present in the body section.

The method ends at 37.

Exemplary implementation of method 30 as performed by the present inventors for the case of breasts of women is shown in FIGS. 8A-B.

Thermospatial representations of two breasts were obtained. For each thermospatial representation a contour was obtained as further detailed hereinabove. The two obtained contours (one for each breast) were compared and a score was calculated to quantify the similarity between the two contours. In the present experiments, the score was calculated as the sum of squares of the mean and standard deviation of the vector of distances between the two contours.

FIG. 8A demonstrates results of an experiment in which the two breasts of the woman subject were devoid of any thermally distinguished. The two obtained contours are illustrated on the same system of coordinates together with a thermospatial representation of the left breast. As shown, the two contours are substantially similar and it can be determined that a thermally distinguished region is not likely to be present in the breasts. The calculated score in this experiment was 230.47.

FIG. 8B demonstrates results of an experiment in which the left breast of the woman subject included a thermally distinguished region and a right breast (of the same woman subject) was devoid of any thermally distinguished region. The two obtained contours are illustrated on the same system of coordinates together with a thermospatial representation of the left breast. As shown, the two contours are substantially dissimilar and it can be determined that a thermally distinguished region is likely to be present in the left breast. The calculated score in this experiment was 1701.64.

Generally, it was found by the inventors of the present invention that when one breast is known to be devoid of a thermally distinguished region, and when the score is the sum of squares of the mean and standard deviation of the vector of distances between the two contours, the method can determine that a thermally distinguished region is likely to be present in the other breast when the score is above 1000. Also contemplated is a comparison between the score for one breast and the score for another breast. If a first breast is known to be devoid of a thermally distinguished region the method can determine that a thermally distinguished region is likely to be present in the second breast if the score of the second breast is significantly higher that than the score of the first breast.

Reference is now made to FIG. 9 which is a flowchart diagram of a method 40 suitable for determining presence or absence of a thermally distinguished region in a body section, according to some embodiments of the present invention.

The method begins at 41 and continues to 42 at which the method determines a thermal signature in the body section, for example, using selected operations of method 10. At 43 the method searches a library of reference thermal signatures for a reference thermal signature which is similar to the thermal signature of the body section.

At 44 the method determines the likelihood of presence of a thermally distinguished region in the body section based on the reference thermal signature found at 43. Specifically, if the reference thermal signature is marked in the library as indicating for presence of thermally distinguished region, the method determines that a thermally distinguished region it is likely to be present. Conversely, if the reference thermal signature is marked in the library as indicating for absence of thermally distinguished region, the method determines that a thermally distinguished region it is not likely to be present. The present embodiments also contemplate estimating the location of a thermally distinguished region. For example, if the method determines that a thermally distinguished region is likely to be present, the method compares the thermal signature to several reference thermal signatures of reference body sections having thermally distinguished region at known locations. The result of these comparisons (e.g., best fit) can be used for estimating the location of the thermally distinguished region in the body section under analysis.

The method ends at 45.

The techniques of the present embodiments can also be implemented for so as to monitor the evolution of a thermally distinguished region in a body section. For example, if the thermal signature is substantially different from its value at an earlier date, the method can determine that the changes in the thermally distinguishable region had occurred. This embodiment can also be useful for monitoring efficacy of treatment. For example, when a subject having a malignant tumor is treated with chemotherapy, the thermal signature can be determined at different times so as to assess the efficacy of treatment.

Reference is now made to FIG. 10 which is a schematic illustration of an apparatus 50 for determining a thermal signature of a body section, according to some embodiments of the present invention. Apparatus 50 can be implemented in a data processor or a computer system and can be used for executing one or more of the method steps described above. Data flow channels between the various components of apparatus 50 are shown as arrows in FIG. 10.

In some embodiments of the present invention apparatus 50 comprises an input unit 52 for receiving the spatial and/or thermal data. For example, input unit 52 can receive a thermospatial representation. Apparatus 50 comprises a segmentation unit 54 for segmenting the thermal data into a plurality of segments, as further detailed hereinabove, and a location calculator 56, for calculating a set of locations defining a contour as further detailed hereinabove. Location calculator 56 receives spatial data from unit 52.

In various exemplary embodiments of the invention apparatus 50 further comprises a weights assigner 58 for assigning weights for at least some picture-elements of the spatial data, as further detailed hereinabove. Weights assigner 58 receives spatial data from unit 52 and provides the weights to location calculator 56.

In some embodiments of the present invention apparatus 50 comprises a slicing unit for slicing the surface to a plurality of slices. In these embodiments, calculator 56 preferably receives the slices from slicing unit 60 and calculates the locations separately for each slice.

In some embodiments of the present invention apparatus 50 comprises a boundary definition unit 62 which defines the spatial boundary between the surface of the body section and the surface of nearby tissue. In these embodiments, location calculator 56, preferably receives data from unit 62 and excludes the surface of the nearby tissue from the calculation of the set of locations. Optionally, boundary definition unit 62 also communicates with slicing unit 60. For example, unit 62 can receive the slices from unit 60 and define the region-of-interest based on the slices. In some embodiments, unit 60 receives the boundaries from unit 62 and calculates the slices after the region-of-interest has been defined.

Apparatus 50 preferably comprises an output unit 64 which issues a report regarding the thermal signature. In some embodiments of the present invention apparatus 50 comprises an analysis unit 66 which compares the thermal signature with a reference thermal signature, as further detailed hereinabove. The analysis unit can access a library of thermal signatures and search the library for a reference thermal signature similar to the thermal signature, as further detailed hereinabove. Analysis unit 66 can employ contour alignment for the purpose of comparison. Analysis unit 66 can provide the results of the comparison to output unit 64, which includes the results in the report. The analysis performed by unit 66 can include the determination of the likelihood that a thermally distinguishable region is present in the body section, as further detailed hereinabove.

Reference is now made to FIG. 11 which is a schematic illustration of an imaging and processing system 70, according to some embodiments of the present invention. System 70 comprises a thermospatial imaging system 72 which provides a thermospatial representation of a body section, and an analysis apparatus 74 for analyzing the thermospatial representation. The principles and operations of analysis apparatus 74 are similar to the principles and operations of apparatus 50 described above. In some embodiments of the present invention apparatus 74 is apparatus 50.

The following description is of techniques for obtaining the thermospatial representation, according to various exemplary embodiments of the present invention. The techniques described below can be employed by any of the method and apparatus described above.

A thermospatial representation or image can be generated obtained by acquiring one or more thermographic images and mapping the thermographic image(s) on a 3D spatial representation.

Figure 12A:
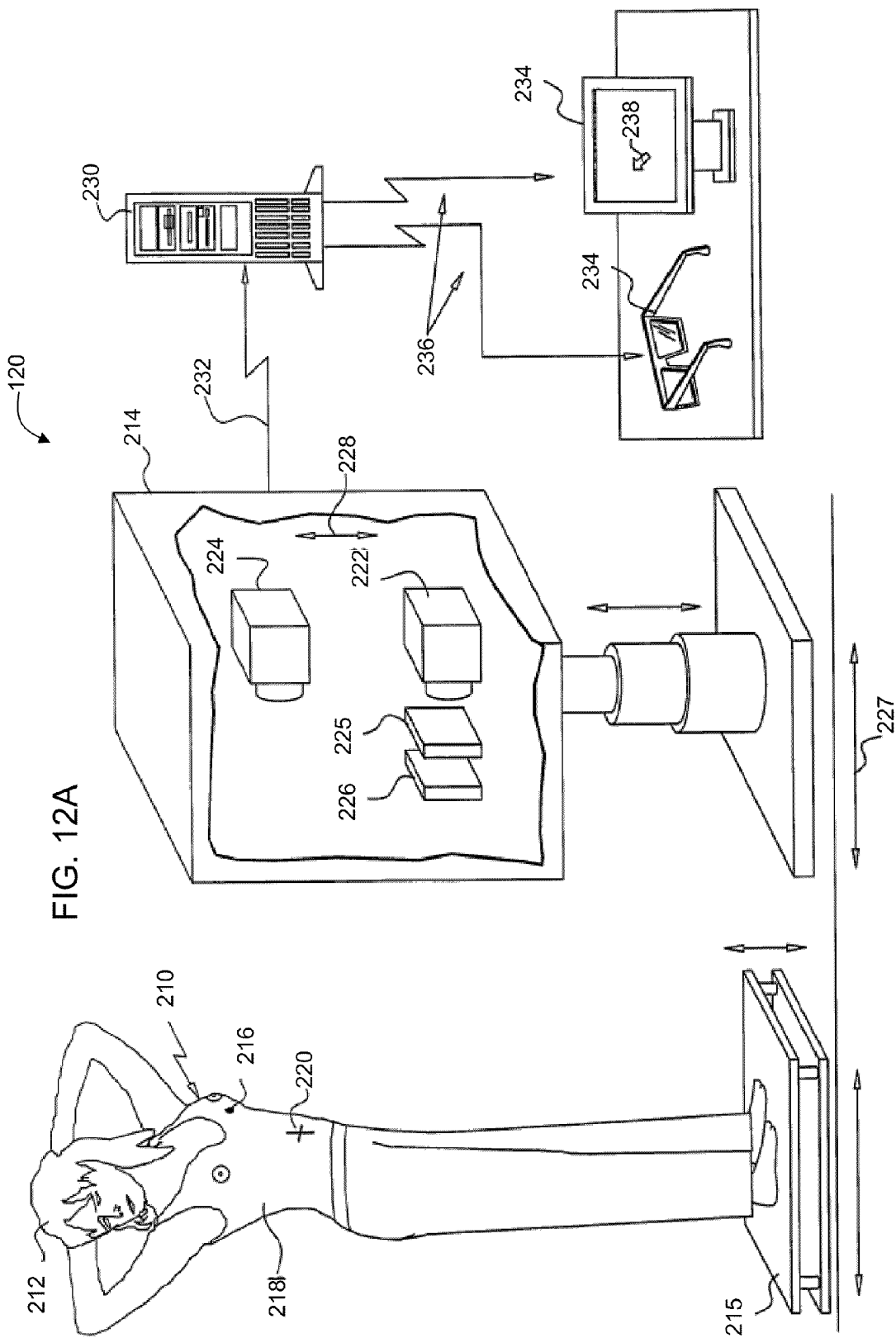

Reference is now made to FIG. 12A which is a schematic illustration of a thermospatial imaging system 120 in accordance with preferred embodiments of the present invention. As shown in FIG. 12A, a living body 210 or a part thereof of a person 212 is located in front of an imaging device 214. The person 212, may be standing, sitting or in any other suitable position relative to imaging device 214. Person 212 may initially be positioned or later be repositioned relative to imaging device 214 by positioning device 215, which typically comprises a platform moving on a rail, by force of an engine, or by any other suitable force. Additionally, a thermally distinguishable object 216, such as a tumor, may exist in body 210 of person 212. For example, when body 210 comprises a breast, object 216 can be a breast tumor such as a cancerous tumor.

In accordance with a preferred embodiment of the present invention, person 212 may be wearing a clothing garment 218, such as a shirt. Preferably, clothing garment 218 may be non-penetrable or partially penetrable to visible wavelengths such as 400-700 nanometers, and may be penetrable to wavelengths that are longer than visible wavelengths, such as infrared wavelengths. Additionally, a reference mark 220 may be located close to person 212, preferably directly on the body of person 212 and in close proximity to body 210. Optionally and preferably, reference mark 220 is directly attached to body 210. Reference mark 220 may typically comprise a piece of material, a mark drawn on person 212 or any other suitable mark, as described herein below.

Imaging device 214 typically comprises at least one visible light imaging device 222 that can sense at least visible wavelengths and at least one thermographic imaging device 224 which is sensitive to infrared wavelengths, typically in the range of as 3-5 micrometer and/or 8-12 micrometer. Typically imaging devices 222 and 224 are capable of sensing reference mark 220 described hereinabove.

Optionally, a polarizer 225 may be placed in front of visible light imaging device 222. As a further alternative, a color filter 226, which may block at least a portion of the visible wavelengths, may be placed in front of visible light imaging device 222.

Typically, at least one visible light imaging device 222 may comprise a black-and-white or color stills imaging device, or a digital imaging device such as CCD or CMOS. Additionally, at least one visible light imaging device 222 may comprise a plurality of imaging elements, each of which may be a three-dimensional imaging element. Device 222 can also comprise a video projector. This embodiment is particularly useful when it is desired to employ the coded light technique (see, e.g., Sato et al, hereinafter) for building a 3D spatial representation.

Optionally and preferably, imaging device 214 may be repositioned relative to person 212 by positioning device 227. As a further alternative, each of imaging devices 222 and 224 may also be repositioned relative to person 212 by at least one positioning device 228. Positioning device 227 may comprise an engine, a lever or any other suitable force, and may also comprise a rail for moving imaging device 214 thereon. Preferably, repositioning device 228 may be similarly structured.

Data acquired by visible light imaging device 222 and thermographic imaging device 224 is output to a data processor 230 via a communications network 232, and is typically analyzed and processed by an algorithm running on the data processor. The resulting data may be displayed on at least one display device 234, which is preferably connected to data processor 230 via a communications network 236. Data processor 230 typically comprises a PC, a PDA or any other suitable data processor. Communications networks 232 and 236 typically comprise a physical communications network such as an internet or intranet, or may alternatively comprise a wireless network such as a cellular network, infrared communication network, a radio frequency (RF) communications network, a blue-tooth (BT) communications network or any other suitable communications network.

In accordance with a preferred embodiment of the present invention display 234 typically comprises a screen, such as an LCD screen, a CRT screen or a plasma screen. As a further alternative display 234 may comprise at least one visualizing device comprising two LCDs or two CRTs, located in front of a user's eyes and packaged in a structure similar to that of eye-glasses. Preferably, display 234 also displays a pointer 238, which is typically movable along the X, Y and Z axes of the displayed model and may be used to point to different locations or elements in the displayed data.

Reference is now made to FIGS. 12B-F and 13A-E which illustrate the various operation principles of thermospatial imaging system 120, in accordance with various exemplary embodiments of the invention.

The visible light imaging is described first, with reference to FIGS. 12B-F, and the thermographic imaging is described hereinafter, with reference to FIGS. 13A-E. It will be appreciated that the visible light image data acquisition described in FIGS. 12B-F may be performed before, after or concurrently with the thermographic image data acquisition described in FIGS. 13A-E.

Referring to FIGS. 12B-F, person 212 comprising body 210 is located on positioning device 215 in front of imaging device 214, in a first position 240 relative to the imaging device. First image data of body 210 is acquired by visible light imaging device 222, optionally through polarizer 225 or as an alternative option through color filter 226. The advantage of using a color filter is that it can improve the signal-to-noise ratio, for example, when the person is illuminated with a pattern or mark of specific color, the color filter can be used to transmit only the specific color thereby reducing background readings. Additionally, at least second image data of body 210 is acquired by visible light imaging device 222, such that body 210 is positioned in at least a second position 242 relative to imaging device 214. Thus, the first, second and optionally more image data are acquired from at least two different viewpoint of the imaging device relative to body 210.

Figure 12B:
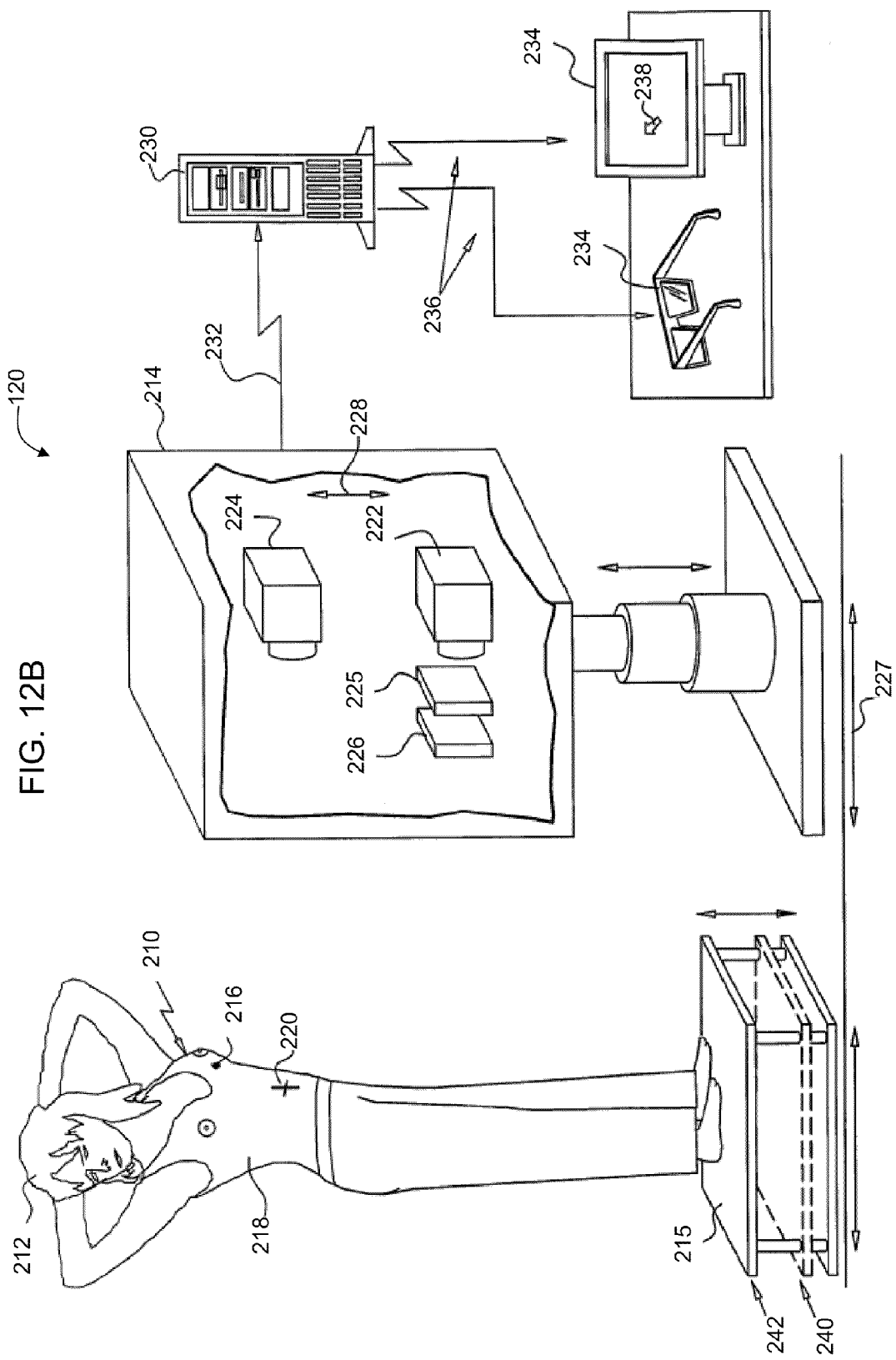
Figure 12C:
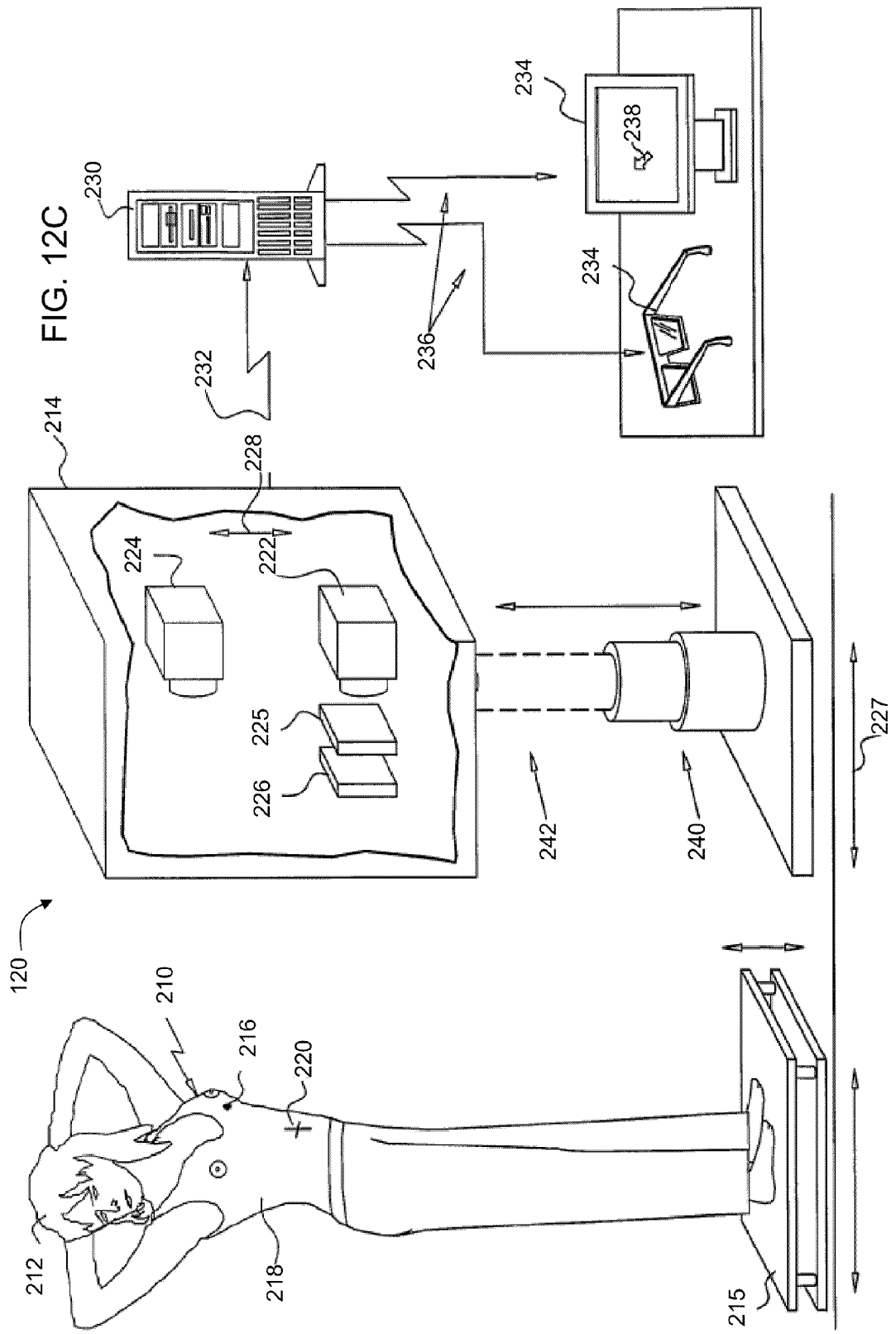
Figure 12D:
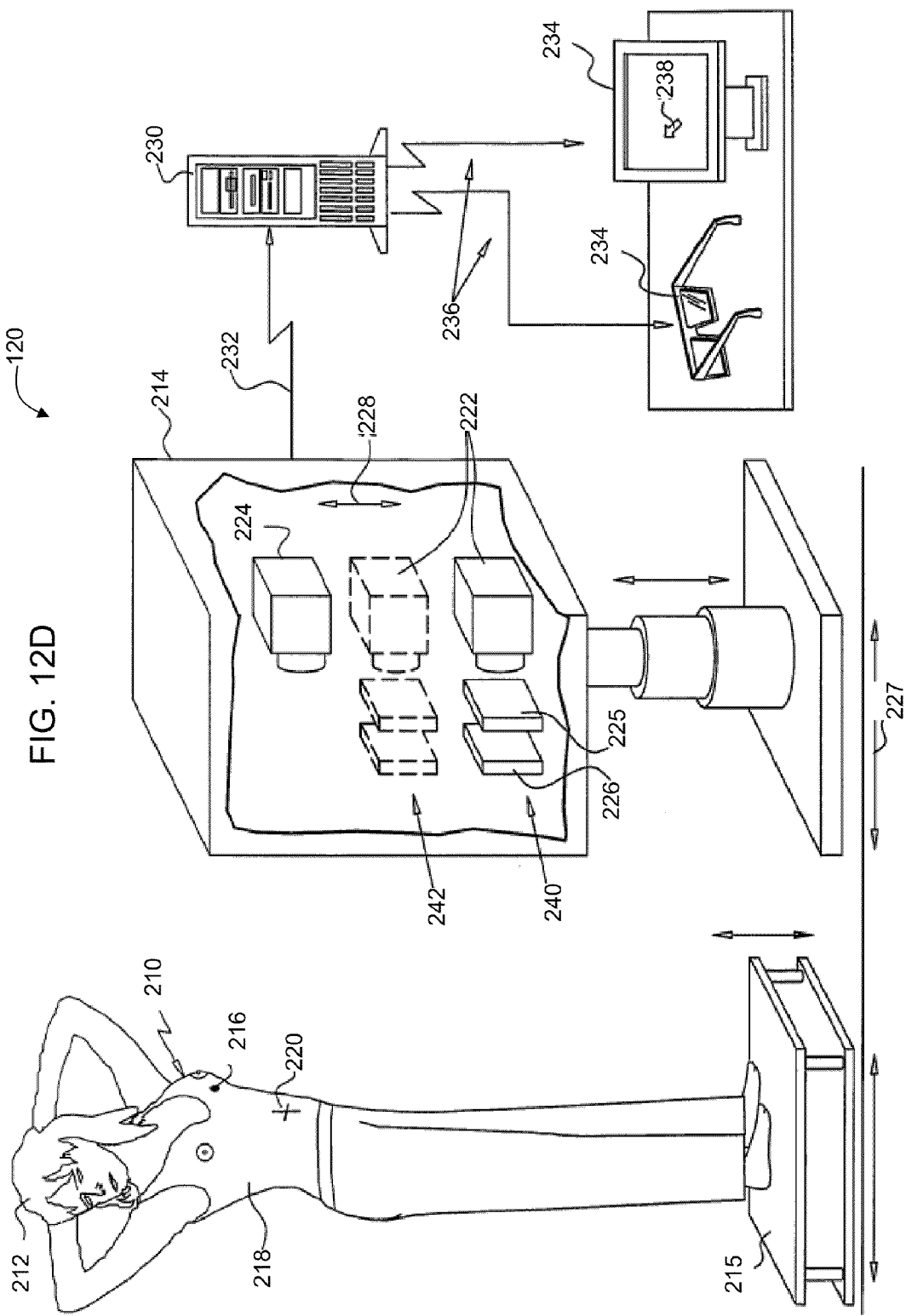
Figure 12F:
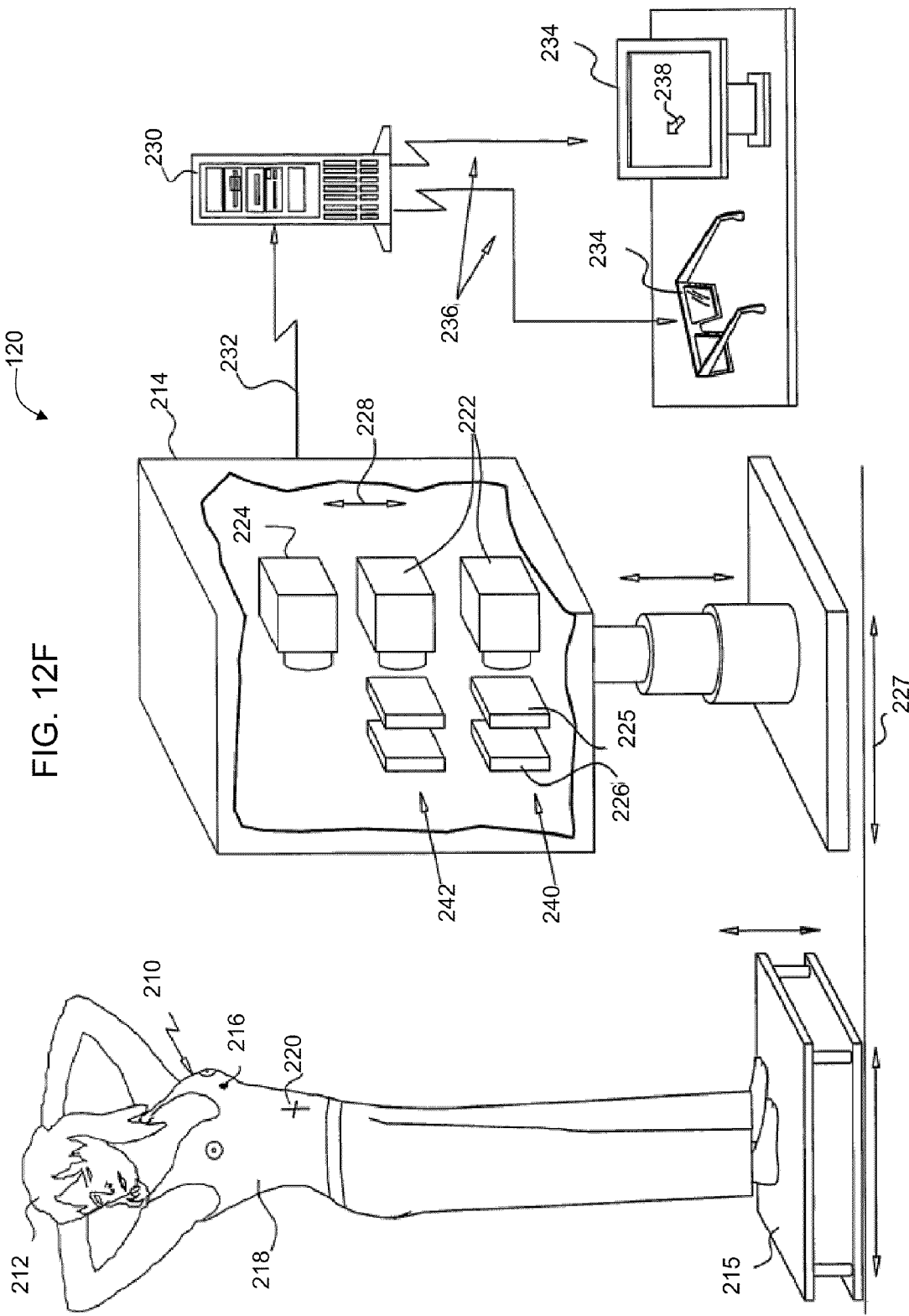

The second relative position 242 may be configured by repositioning person 212 using positioning device 215 as seen in FIG. 12B, by repositioning imaging device 214 using positioning device 227 as seen in FIG. 12C or by repositioning imaging device 222 using positioning device 228 as seen in FIG. 12D. As a further alternative, second relative position 242 may be configured by using two separate imaging devices 214 as seen in FIG. 12E or two separate visible light imaging device 222 as seen in FIG. 12F.

Referring to FIGS. 13A-E, person 212 comprising body 210 is located on positioning device 215 in front of imaging device 214, in a first position 244 relative to the imaging device. First thermographic image data of body 210 is acquired by thermographic imaging device 224. Optionally and preferably at least second thermographic image data of body 210 is acquired by thermographic imaging device 224, such that body 210 is positioned in at least a second position 242 relative to imaging device 214. Thus, the first, second and optionally more thermographic image data are acquired from at least two different viewpoints of the thermographic imaging device relative to body 210.

Figure 13B:
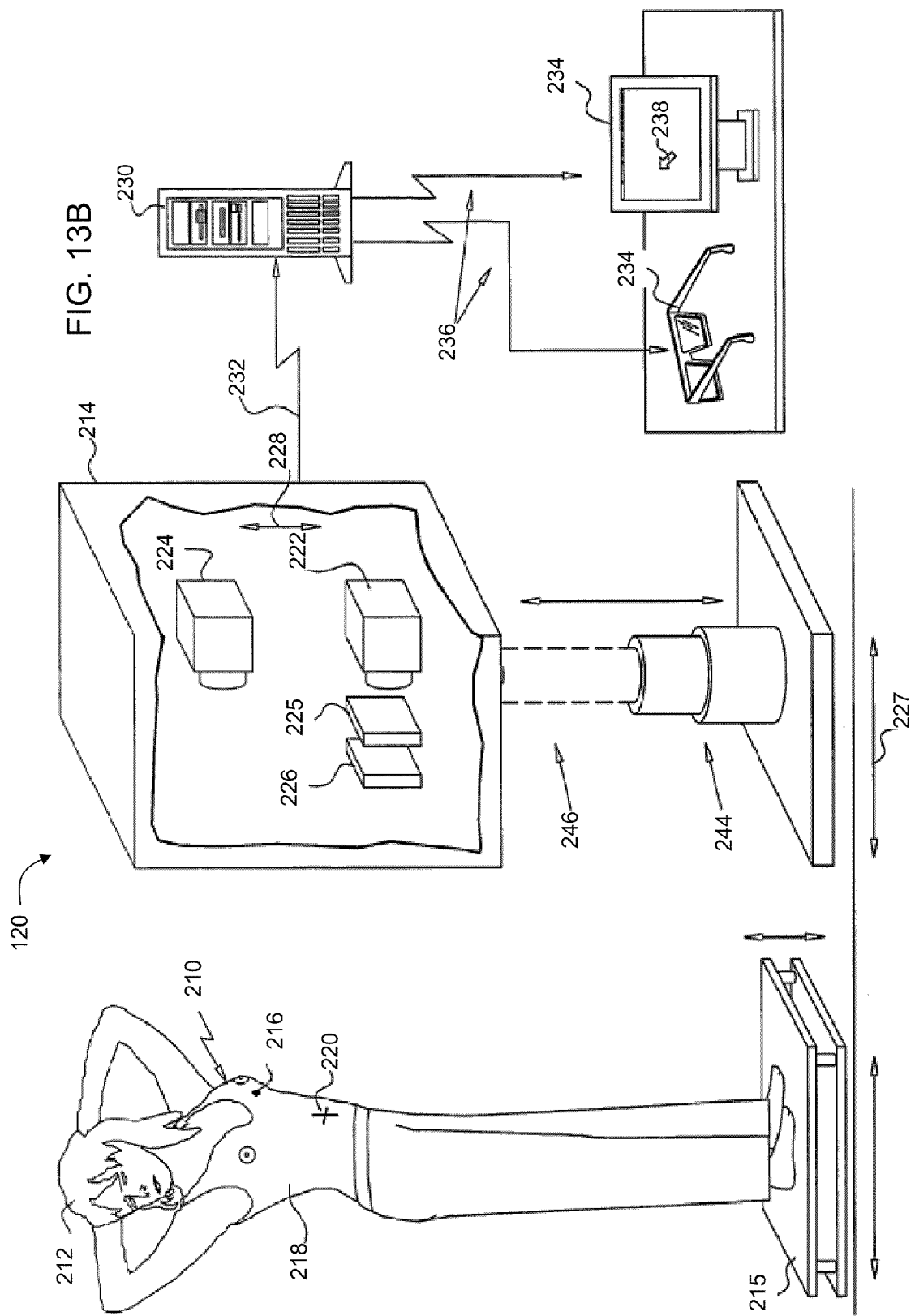
Figure 13C:
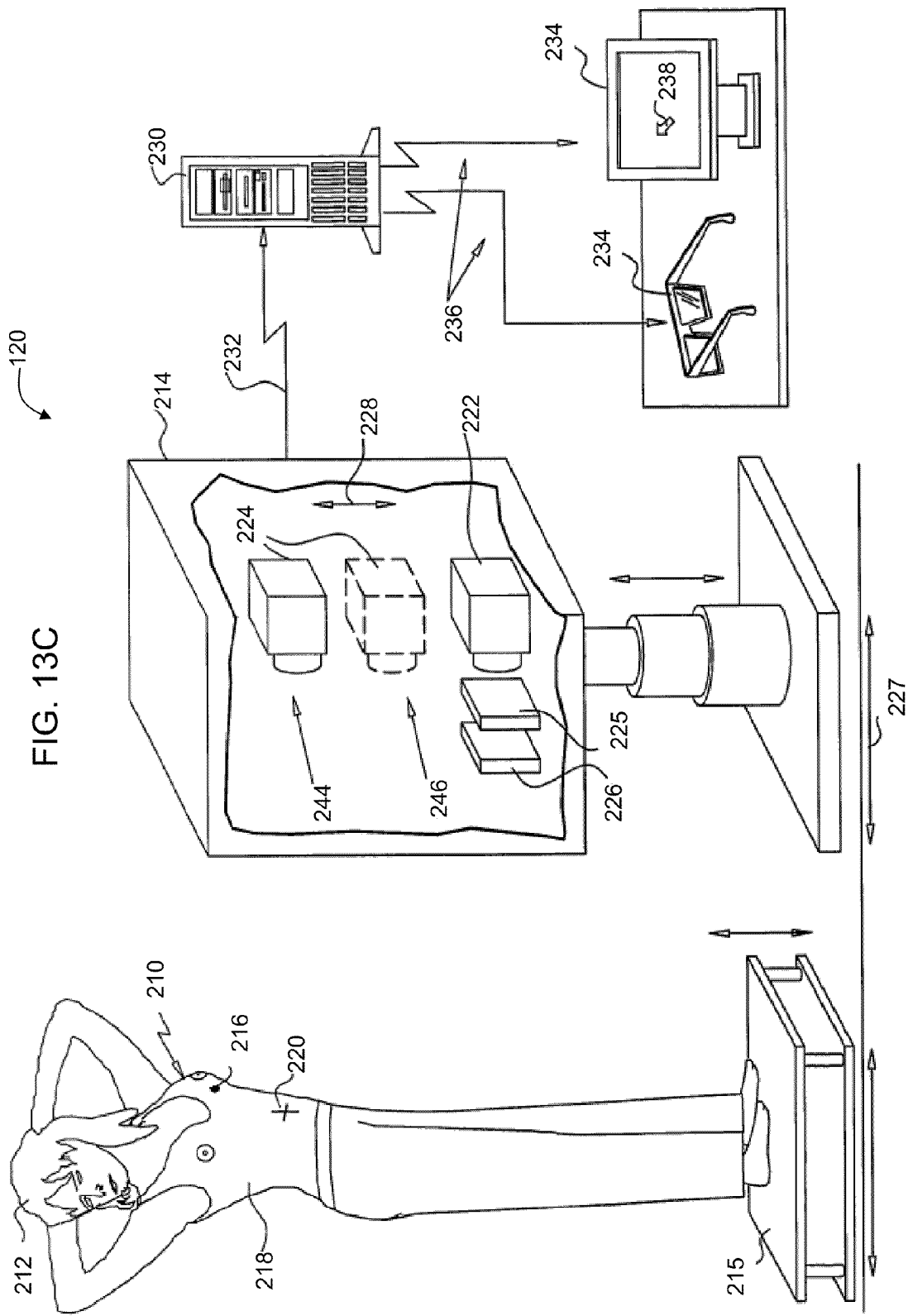
Figure 13E:
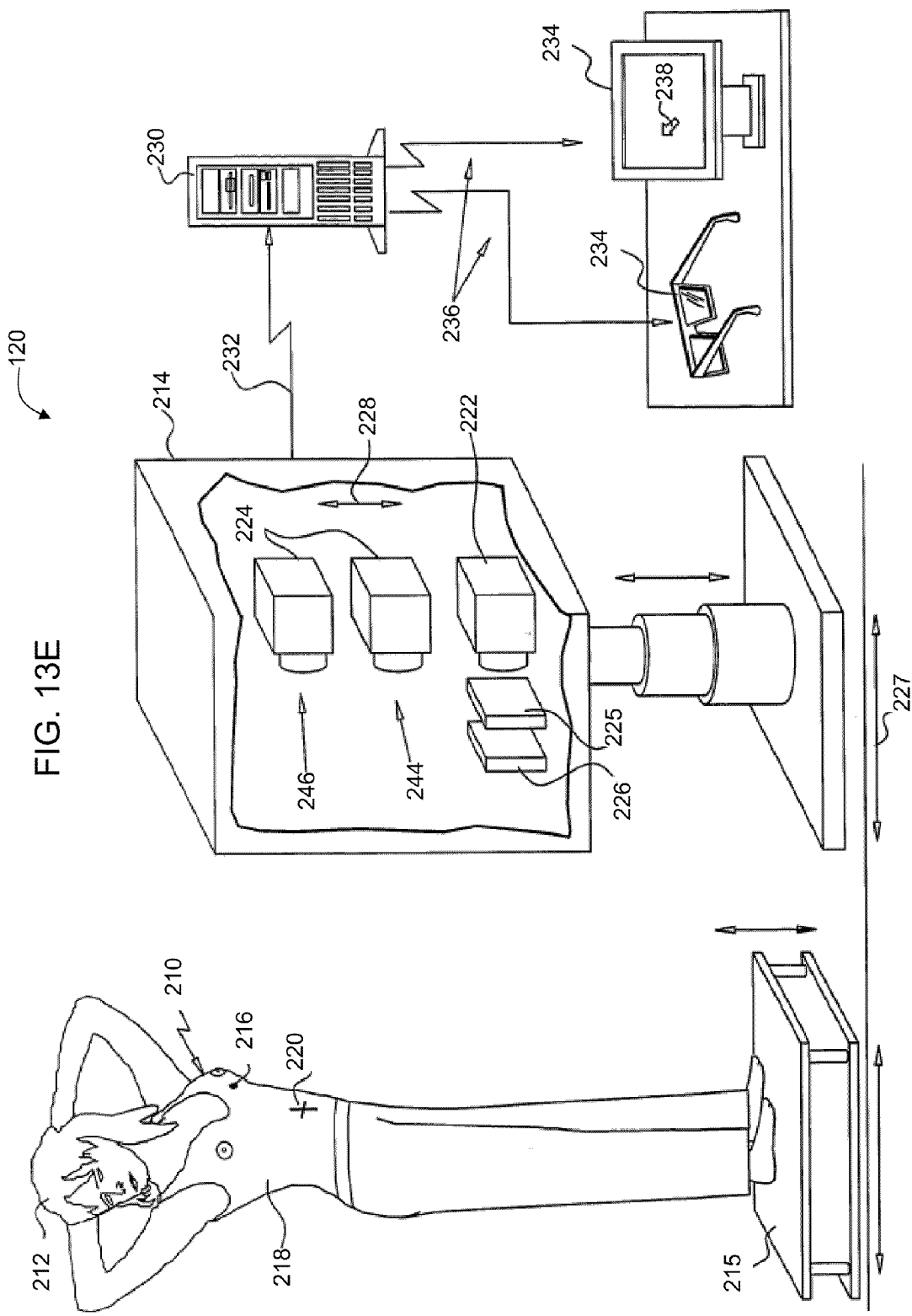

The second relative position 246 may be configured by repositioning person 212 using positioning device 215 as seen in FIG. 13A, by repositioning imaging device 214 using positioning device 227 as seen in FIG. 13B, or by repositioning thermographic imaging device 224 using positioning device 228 as seen in FIG. 13C. As a further alternative, the second relative position 246 may be configured by using two separate imaging devices 214 as seen in FIG. 13D or two separate thermographic imaging devices 224 as seen in FIG. 13E.

Image data of body 210 may be acquired by thermographic imaging device 224, by separately imaging a plurality of narrow strips of the complete image of body 210. Alternatively, the complete image of body 210 is acquired by the thermographic imaging device, and the image is sampled in a plurality of narrow strips or otherwise shaped portions for processing. As a further alternative, the imaging of body 210 may be performed using different exposure times.

The thermographic and visible light image data obtained from imaging device 214 is preferably analyzed and processed by data processor 230 as follows. Image data acquired from imaging device 222 is processed by data processor 230 to build a three-dimensional spatial representation of body 210, using algorithms and methods that are well known in the art, such as the method described in U.S. Pat. No. 6,442,419 or Sato et al., "Three-dimensional Surface Measurement by Space Encoding Range Imaging, Journal of Robotic Systems (1985) 27-39, the contents of which is hereby incorporated by reference as if fully set forth herein. The 3D spatial representation preferably comprises the location of reference marker 220 (cf. FIG. 1A). Optionally and preferably, the 3D spatial representation comprises information relating to the color, hue and tissue texture of body 210. Thermographic image data acquired from imaging device 224 is processed by data processor 230 to build a thermographic three-dimensional model of body 210, using algorithms and methods that are well known in the art, such as the method described in U.S. Pat. No. 6,442,419. The thermographic 3D model preferably comprises reference marker 220 (cf. FIG. 1B). The thermographic 3D model is then mapped by processor 230 onto the 3D spatial representation, e.g., by aligning reference marker 220, to form the thermospatial image.

The present embodiments are also useful for constructing blood vessels map or for determining the location a specific blood vessel within the body because the temperature of the blood vessel is generally different from the temperature of tissue. In this respect, the present embodiments are also useful in the area of face recognition, because the knowledge of blood vessel positions in the face may aid in the identification of certain individuals. Recognition of other organs is also contemplated. Organ recognition using the present embodiments is particularly advantageous due to the ability of the present embodiments to localize thermally distinguishable regions in the living body. Such localization can be used for constructing blood vessel map which provides information regarding both orientation and depth of blood vessels in the body. The map can then be used for identifying individuals, e.g., by searching for similar map on a accessible and searchable database of blood vessel maps. The map can also be an additional indicator for existence and/or location of tumors in the body section.

Reference is now made to FIG. 14 which is a flowchart diagram of a method 300 suitable for identifying blood vessels in a thermal image of a section of a living body. The method begins at 310 and continues to 320 at which the method performs convolution of intensity data representing the thermal image (e.g., intensity data, variance, changes over time, etc.) with a predetermined vessel shapes filter thereby providing filtered data.

The present inventors have investigated the form of several blood vessels that appear in different areas of the body. By comparing the correlation coefficient between all pattern samples, the present inventor successfully defined several types of vessel patterns. The predetermined vessel shapes filter of the present embodiments includes this information. In some embodiments of the present invention the method convolves the rows and columns of the thermal image with a matrix of a vessel pattern. Typically, the vessel pattern matrix is a 4×4 matrix, but other sizes of matrices are not excluded from the scope of the present invention.

At 330 the method calculates local derivatives of the filtered data along at least two dimensions to providing derivative data. The local derivatives are typically with respect to the lateral dimensions (the x and y dimensions in the present coordinate-system). In various exemplary embodiments of the invention the derivatives are calculated separately for each dimension, and the method selects the highest derivative for each picture-element of the thermal image. The procedure can be described as follows. Firstly, the derivative is implemented in one direction (say the x direction) to provide a first derivative image. Secondly, the derivative is implemented in another direction (say the y direction) to provide a second derivative image. Thirdly, the method compares the two images pixel-by-pixel and selects the highest of the two derivatives for each pixel. It was found by the present inventors that this operation can reveal the morphology of blood vessels in the thermal image. This operation provides a morphology which can be described as a system of ridges (local maxima) that divides areas drained by different grooves (local minima) as blood vessels.

At 340 the method searches the derivative data for local intensity extrema, and at 305 the method applies an interpolation procedure for generating contours between at least a few of the local intensity extrema. In various exemplary embodiments of the invention the generated contours are identified as blood vessels.

The method ends at 350.

In some embodiments of the present invention method 300 comprises one or more additional operations. These embodiments will now be explained with reference to FIGS. 15, 16A-I, 17A-C and 18.

Figure 16A:
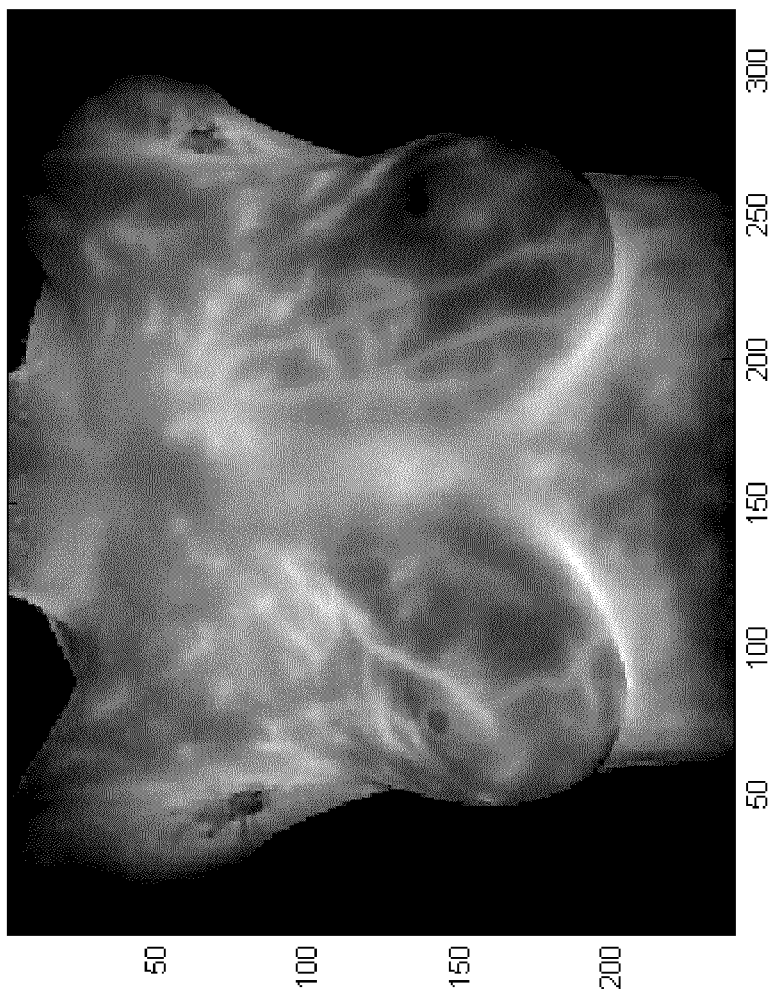

FIG. 15 is a flowchart diagram describing method 300 according to some embodiments of the present invention. The method begins at 310 and optimally continues to 311 at which the intensity data is normalized. The normalization can be according to any scheme known in the art. In various exemplary embodiments of the invention mean normalization is employed. In these embodiments, the global mean of the all image is subtracted from each picture-element of the image. Also contemplated are: subtraction or division of global minimum or maximum, midrange preserving normalization, and the like. The result of mean normalization is shown in FIG. 16A in the form of a two-dimensional image.

Figure 16B:
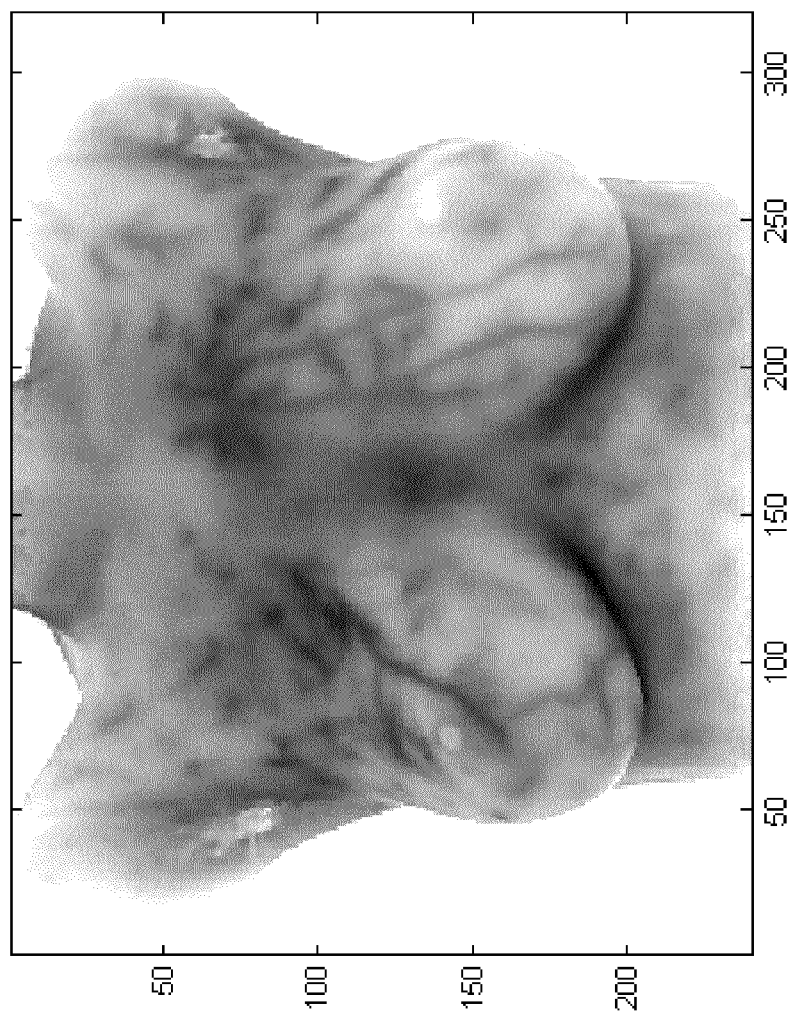

The method optionally continues to 312 at the method inverts the intensity data by linear transformation. This operation is known in the art and includes the transformation I→$I_{max}$–I, where I is the intensity value and $I_{max}$ is the maximal intensity value. In embodiments in which the normalization operation is performed, I is the normalized intensity and $I_{max}$ is the maximal normalized intensity. The result of the inversion operation is shown in FIG. 16B in the form of a two-dimensional image.

The method optionally continues to 313 at which the method masks the intensity data so as to exclude at least a portion of the intensity data, where the excluded portion corresponds to picture-elements not belonging to blood vessels. In embodiments in which normalization is preferably employed the masking operation is performed on the normalized data. The masking can be done by calculating at least one of: local minimum, local maximum and local average for each picture-element of the thermal image. These local quantities are preferably calculated using the intensity values of the picture-element and at least a few of its neighbors.

Figure 17A:
Figure 17B:
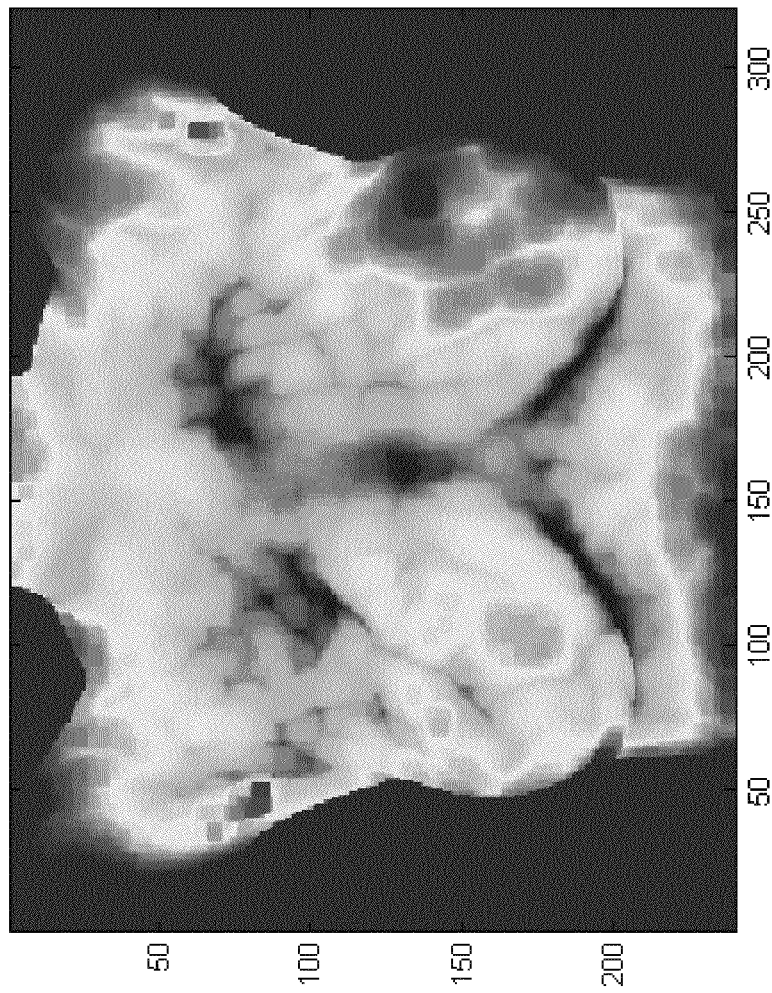
Figure 17C:
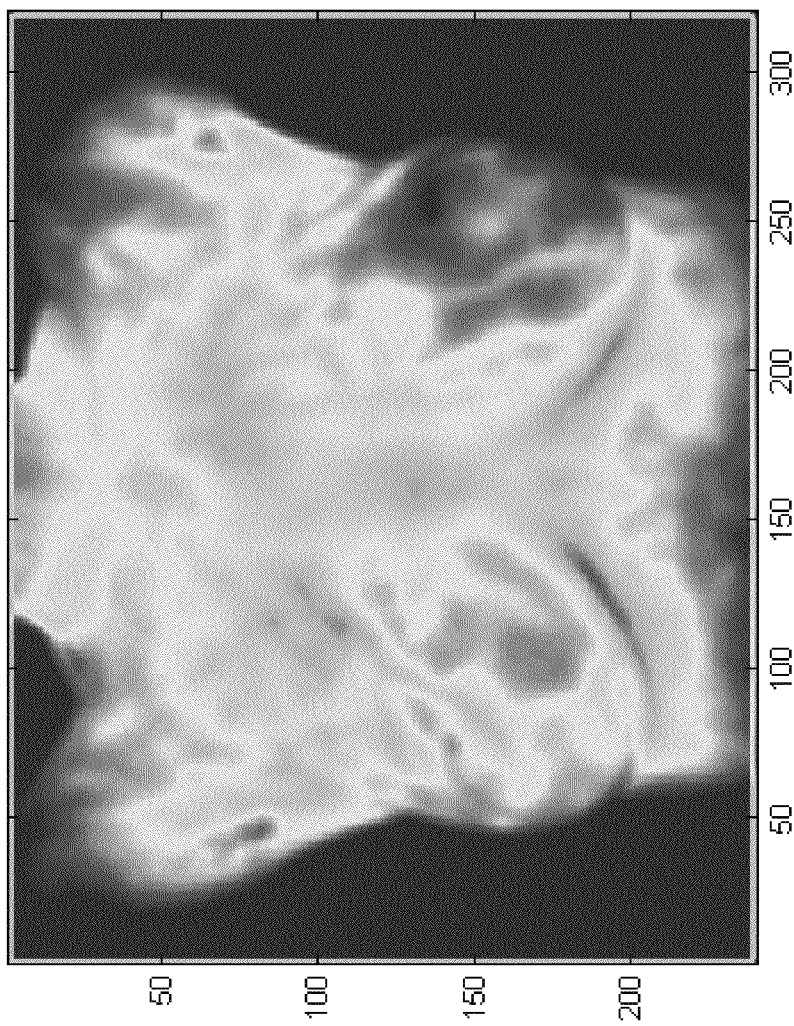

In various exemplary embodiments of the invention a moving window scans the image. At each location of the moving window, one or more local statistical quantities such as, but not limited to, minimum intensity, maximum intensity and mean intensity are calculated over the window and are assigned to the picture-element located at the center of the window. The procedure results in one statistical image per calculated quantity, where in each image, each picture-element contains the calculated value of the respective quantity. FIGS. 17A-C show statistical images obtained after calculation of local minimum (FIG. 17A), local maximum (FIG. 17B), and mean (FIG. 17C) for a 3×3 moving window. Other sizes of moving windows are also contemplated.

The masking can also include calculation of global quantities, such as, but not limited to, global minimum, global maximum and global mean values for each of the statistical images. In various exemplary embodiments of the invention a set of comparisons queries between the values of the global quantities and the three statistical images, normalized and negative image to provide a binary masking image in which picture-element that are candidate for belonging to a blood vessel are marked. For example, the binary masking image can includes 1's and 0's where candidate picture-elements are assigned with 1's while all other picture-element are assigned with 0's. Typically the masking image does not include edge values that usually belong to background or skin folds.

Following are some exemplified embodiments for the construction of the masking image. Each of the exemplified embodiments below can be employed either singly or in combination with one or more other embodiments. The employment of all the exemplified embodiments below is also contemplated. The embodiments below are provided only for illustrative purposes and should not be construed in any limiting way. In fact, those reasonably skilled in the art of image processing will understand that the masking image can be constructed using other procedures or combination of procedures.

In some embodiments of the present invention a picture-element in the masking image is assigned with "1" if the intensity value of a corresponding picture-element in the local minimum image is below a predetermined threshold. Such threshold can be approximately or a few percents below the global maximum value of the local minimum image.

In some embodiments of the present invention a picture-element in the masking image is assigned with "1" if the intensity value of a corresponding picture-element in the local maximum image is below a predetermined threshold. Such threshold can be approximately or some percents above the global mean of the local maximum image.

In some embodiments of the present invention a picture-element in the masking image is assigned with "1" if the intensity value of a corresponding picture-element in the mean image is below a predetermined threshold. Such threshold can be approximately or some percents above the global mean of the local minimum image.

In some embodiments of the present invention a picture-element in the masking image is assigned with "1" if the intensity value of a corresponding picture-element in the mean image is above a predetermined threshold. Such threshold can be approximately the global minimum of the local maximum image.

In some embodiments of the present invention a picture-element in the masking image is assigned with "1" if the intensity value of a corresponding picture-element in the inverted image is below a predetermined threshold. Such threshold can be approximately the intensity value of a corresponding picture-element in the local maximum image.

In some embodiments of the present invention a picture-element in the masking image is assigned with "1" if the intensity value of a corresponding picture-element in the normalized image is within a predetermined threshold. Such threshold can be approximately or a few percents above the minimal intensity value of the normalized image.

In some embodiments of the present invention a picture-element in the masking image is assigned with "1" if the intensity value of a corresponding picture-element in the normalized image is within a predetermined threshold. Such threshold can be approximately or several times the mean intensity value of the normalized image.

Figure 16C:

FIG. 16C shows the obtained masking image, in embodiments in which the statistical images of FIGS. 17A-C as well as their global minimum, maximum and mean values are employed during the masking operation.

Figure 16D:
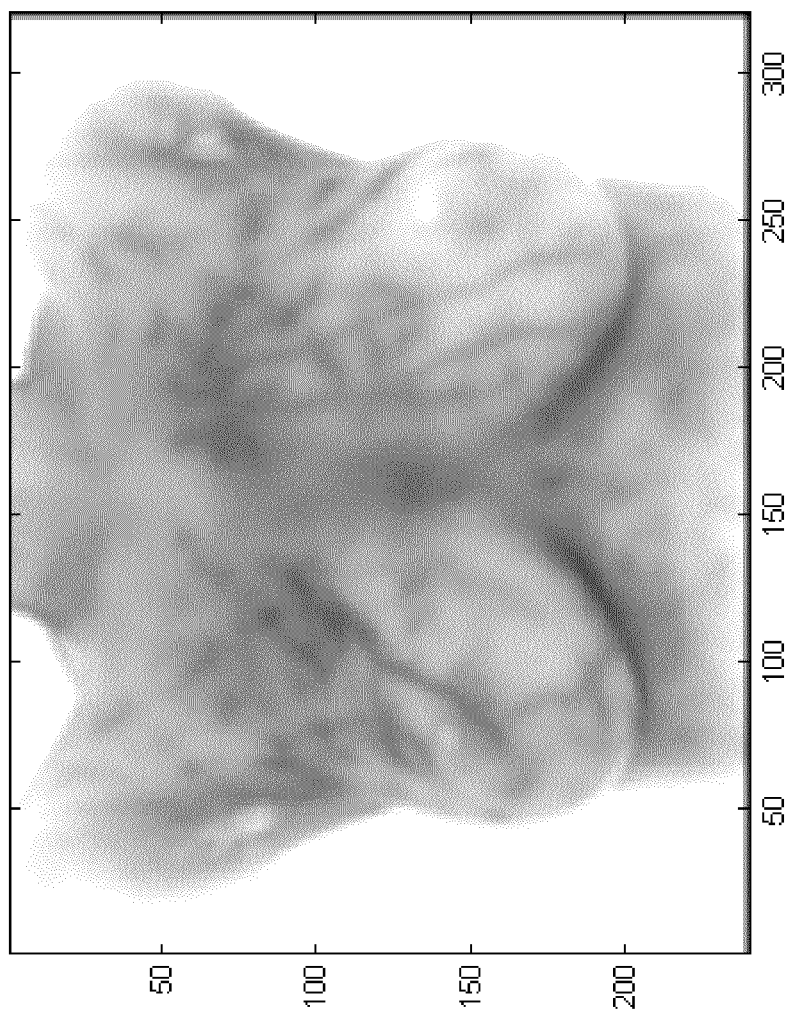

At 320 the method performs convolution with a predetermined vessel shapes filter as further detailed hereinabove. In embodiments in which inversion is employed, the convolution operation is preferably performed on the inverted intensity data. The advantage of operating on the inverted data is that is provides better visualization. FIG. 16D shows the result of the convolution in the form of a two-dimensional image, in the embodiments in which the vessel shapes filter is convoluted with the inverted intensity data.

Figure 16E:
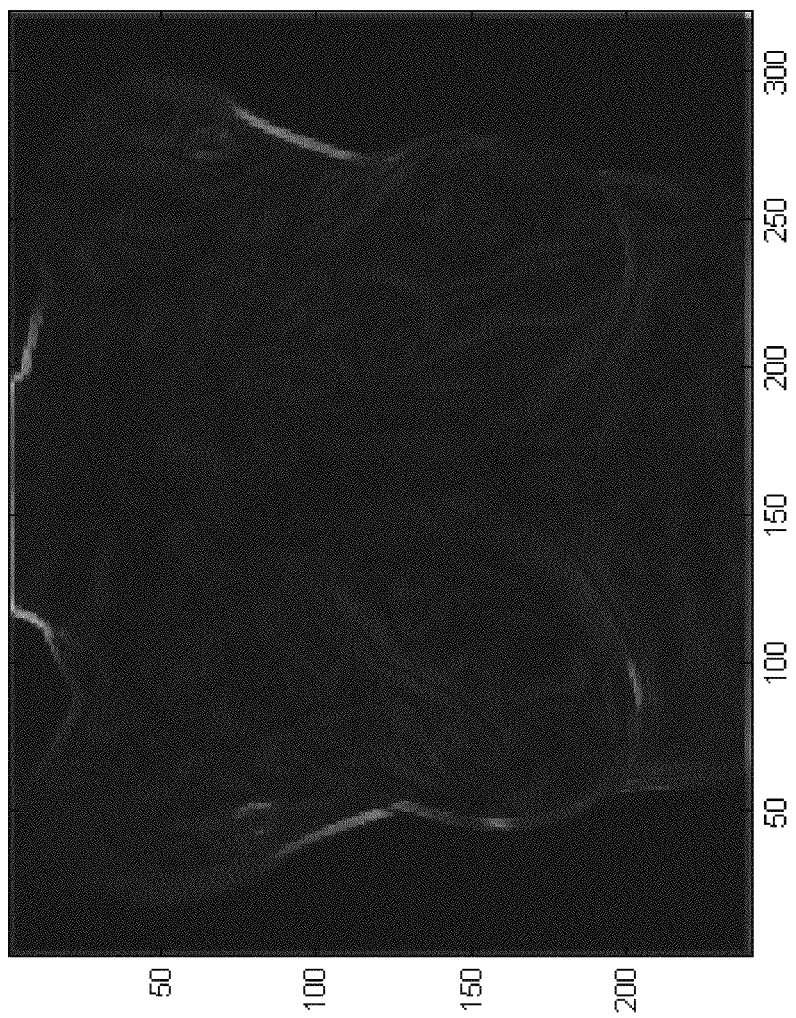

At 330 the method calculates local derivatives of the filtered data along at least two dimensions as further detailed hereinabove. FIG. 16E shows the local derivative data of FIG. 16D in a form of a two-dimensional image.

At 340 the method searches the derivative data for local intensity extrema. When the convolution with the vessel shapes filter is performed using the inverted data, the method preferably searches for local intensity minima. When the convolution with the vessel shapes filter is performed using the inverted data, the method preferably searches for local intensity maxima. When a masking image is constructed, the method preferably perform the search only among picture-element which are marked by the masking image as candidates for belonging to a blood vessel.

The search preferably employs a moving window, e.g., a 3×3 moving window which allows comparison of the intensity value of each picture-element with the intensity values of its eight immediate neighbors. Other sizes of moving window are also contemplated.

The search for extrema can be accompanied by a set of criteria. In some embodiments of the present invention the method calculates gradients of intensities over a range of picture-element in the vicinity of the picture-element under analysis and decides, based on the gradient, whether the picture-element is at a local extremum of intensities. Typical range for the calculation of gradients is about four picture-elements from the picture-element under analysis. A procedure according to some embodiments of the present invention can be better understood with reverence to FIG. 18 which is a fragmentary schematic illustration of a rectangular grid of picture-elements. The ordinarily skilled person would know how to adjust the description to non-rectangular grids which are not excluded from the scope of the present invention.

Shown in FIG. 18 is a central picture-element 400 which is the picture-element under analysis, and other picture-elements in the vicinity of element 400. Also shown in FIG. 18 is a two-dimensional Cartesian coordinate-system. The four nearest neighbors to element 400 (along the x and y directions) are designated by reference sign 401, the four next-to-nearest neighbors picture-element (nearest neighbors along a diagonal) are designated by reference sign 402. Picture-elements in a layer immediately surrounding elements 401 and 402 are designated by reference signs 403, 404 and 405, where higher reference numerals correspond to higher distance from the element under analysis (element 400). Picture-elements in the next layer (immediately surrounding elements 403-405) are designated by reference sign 406.

According to some embodiments of the present invention the method determines that there is a local minimum of intensity at the location of element 400 if at least one, and more preferably each of the following criteria is met: (i) the intensity of element 400 is higher than the intensity of element 401; and (ii) the intensity value of element 400 is higher than the intensity of element 403 divided by k, where k is a predetermined threshold. A typically value of k is between 1 and 2, e.g., 1.5.

In various exemplary embodiments of the invention adjacent picture-element having identical intensity are checked to be local minimum in all eight directions. For example, suppose that the intensities of the two elements which are marked by rectangle 420 in FIG. 18 (element 400 and its nearest immediate neighbor 401 from the right side) are equal. In this case the method according to the present embodiment decides that there is a local minimum at the location 400 if the intensity value of element 400 is lower than the intensity values of each of the 10 elements in the immediate layer surrounding those two elements (the layer of picture-element between rectangle 420 and rectangle 422).

Figure 16F:
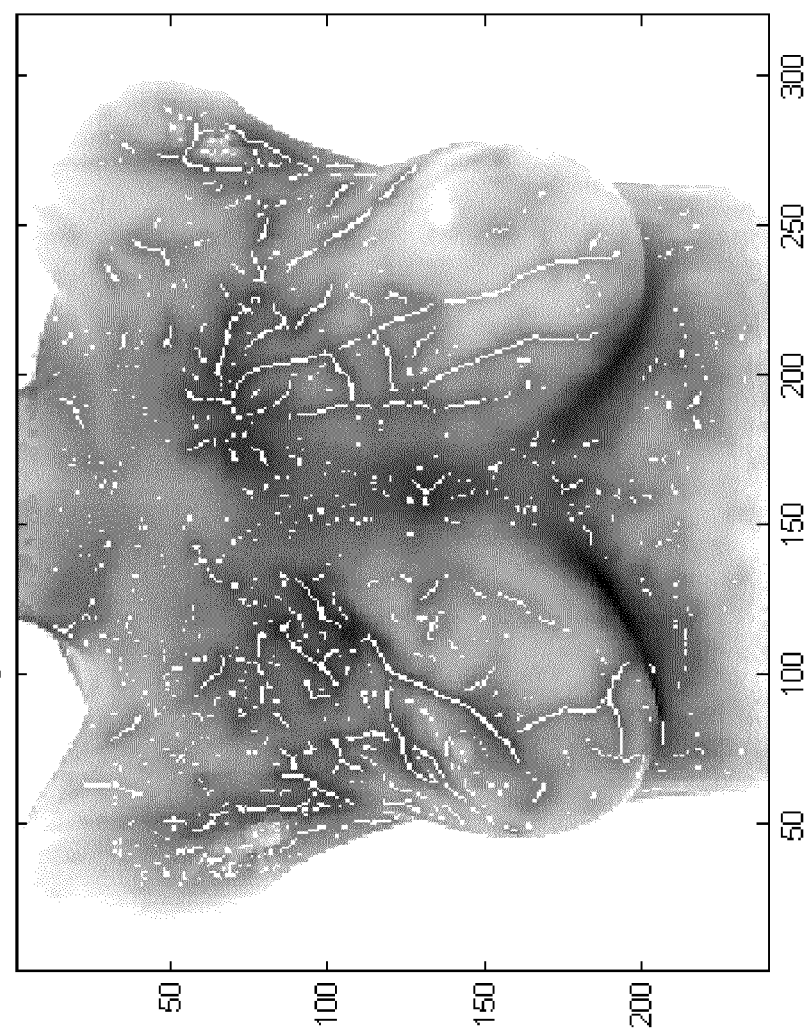

FIG. 16F shows patterns of local minima in the form of a two-dimensional image, in the embodiments in which the above search procedure is employed.

Figure 16G:
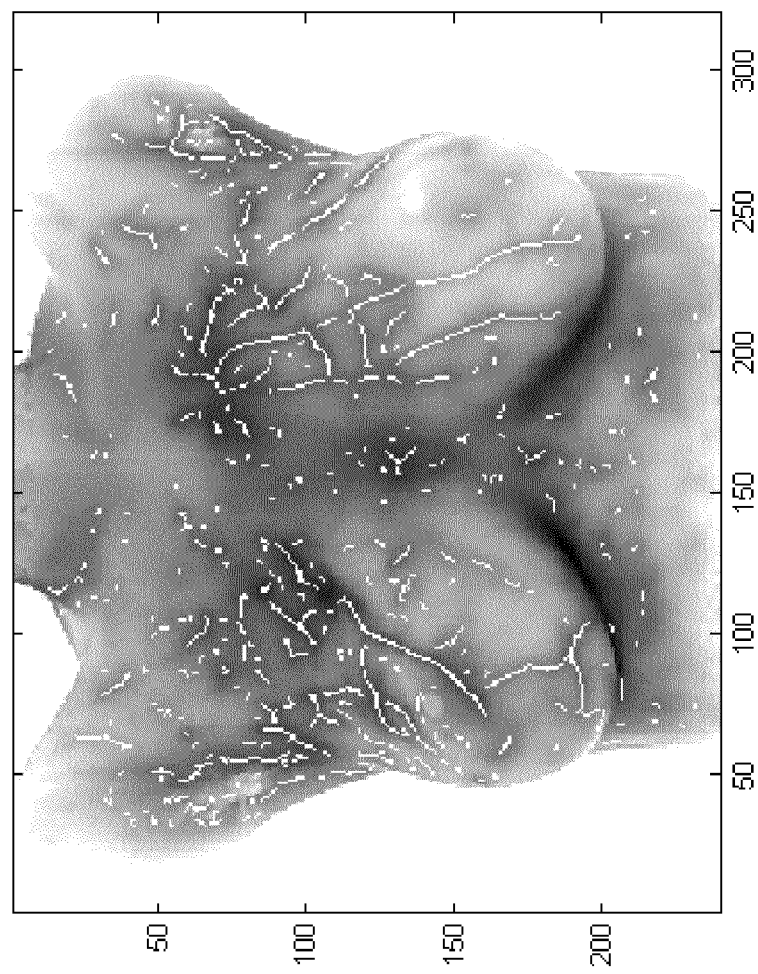

Optionally, the method continues to 341 at which the method employs a noise reduction procedure. This can be done, for example, by searching for picture-elements which are identified as located in local exterma but which are isolated from other local extrema. These elements are preferably declared by the method as noise. In various exemplary embodiments of the invention noise picture-elements are assigned with their original intensity. FIG. 16G shows patterns of local minima in the form of a two-dimensional image, after the implementation of a noise reduction procedure of the present embodiments.

Figure 16H:
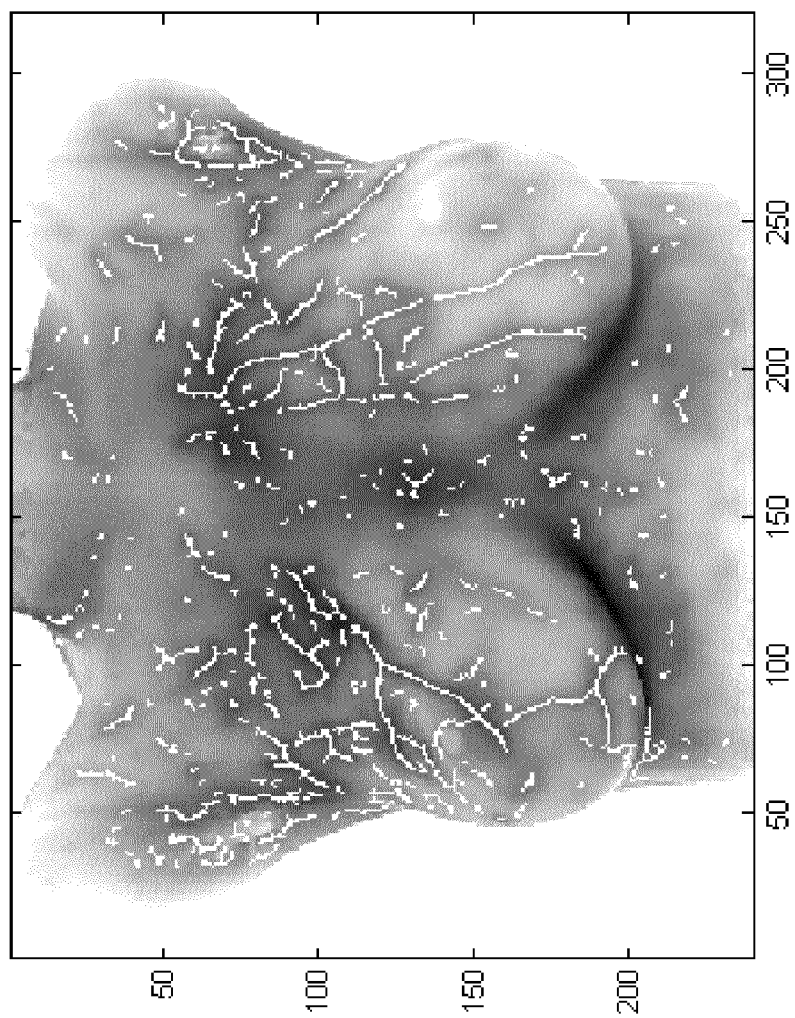

At 350 the method applies an interpolation procedure for generating contours between at least a few of the local intensity extrema. The method preferably searches the local extrema and decides according to a predetermined criterion or set of criteria whether or not to join non-continuous segments of local extrema. For example, the method can connect two local intensity extrema if the distance between them is not higher than two pixels. FIG. 16H shows patterns of local minima in the form of a two-dimensional image, after the implementation of the noise reduction procedure followed by the interpolation procedure of the present embodiments.

In various exemplary embodiments of the invention the generated contours are identified as blood vessels. The method preferably issues a report which includes the identified blood vessels. FIG. 16-I is an example of a report which is in the form of a two-dimensional image showing the patterns of the identified blood vessels. The identified blood vessels can also be presented as a map of blood vessels.

It is to be understood that the presentation and reference to "images" in the above description is for the purpose of clarity and is not to be considered as limiting. The method of the present embodiments can be implemented without displaying the data resulting from each operation in the form of an image. Yet, the presentation of an image for at least a few of the operations is not excluded from the scope of the present invention.

Method 300 ends at 350.

Reference is now made to FIG. 19 which is a schematic illustration of an apparatus 500 for identifying blood vessels in a thermal image of a section of a living body, according to some embodiments of the present invention. Apparatus 500 can be implemented in a data processor or a computer system and can be used for executing one or more of the method steps described above. Preferred data flow channels between the various components of apparatus 500 are shown as arrows in FIG. 19. It is to be understood, however, that some data flow channels are optional and may be omitted, for example, and that the method also contemplates other data flow channels which, for clarity of presentation, are not shown in FIG. 19.

In some embodiments of the present invention apparatus 500 comprises an input unit 502 for receiving the thermal image. Apparatus 500 preferably comprises a convolution unit 504 which convolves the intensity data with a predetermined vessel shapes filter, a derivative calculator 506 which calculates local derivatives of the filtered data, a local intensity extrema searcher 508 which searches in the derivative data for local intensity extrema, and an interpolator 510 which applies an interpolation procedure for generating contours between at least a few of the local intensity extrema, and identifying the contours as blood vessels as further detailed hereinabove.

In some embodiments of the present invention apparatus 500 comprises a normalization unit 512 which normalizes the intensity data, as further detailed hereinabove. In some embodiments of the present invention apparatus 500 further comprises an intensity data inverter 514 for inverting the intensity data by linear transformation, as further detailed hereinabove. In some embodiments of the present invention apparatus 500 comprises a masking unit 516 for masking the intensity data so as to exclude at least a portion of the intensity data, as further detailed hereinabove. In some embodiments of the present invention apparatus 500 comprises a noise reduction unit 518 which employs a noise reduction procedure to exclude isolated local intensity extrema, as further detailed hereinabove.

Apparatus 50 preferably comprises an output unit 520 which issues a report regarding the patterns and locations of the identified blood vessels. The report can be in the form of an image or a blood vessel map as further detailed hereinabove.

Identification of blood vessels according to some embodiments of the present invention can be useful for the estimation of characteristic heat conduction of a body section. For example, when a series of thermospatial representations of the body section are known, the present embodiments can calculate the depth of one or more blood vessel sections and measure the rate of heat transfer to or from the blood vessel section(s).

FIG. 20 is a flowchart diagram of a method suitable for estimating characteristic heat conduction, according to various exemplary embodiments of the present invention.

The method begins at 600 and continues to 601 at which a first data acquisition (spatial and thermal) is performed while the body section is in a first shape referred to hereinafter as the "undeformed shape." The method continues to 602 at which a first thermospatial representation is constructed, and 603 at which the depth of one or more blood vessel sections is calculated using the first thermospatial representation. Calculation of depth from the thermospatial representation can be done, for example, by triangulation or any other technique known in the art.

The method subsequently proceeds to 604 in which a second data acquisition is performed while the body section is in a second shape which is deformed with respect to the undeformed shape. A second thermospatial representation is then constructed. While the shape is still deformed, data is repeatedly acquired until the blood vessels section(s) is in a steady thermal state (decision 605). The repetition of data acquisition (process 604) can be done only for thermal data since there is no change in the shape of the body section between successive acquisitions.

The method continues to 606 at which the thermal stabilization period is determined. Generally, the thermal stabilization period can be defined as the elapsed time between the deformation of the body shape and the onset of steady state. The method can also calculate the difference in steady state temperatures before and after deformation. The method proceeds to 607 in which the second thermospatial representation is used for recalculating the depth of the same blood vessel section(s) so as to determine the difference in the depths due to the deformation. The method then continues to 608 at which the thermal conductivity is calculated based at least in part on the knowledge of the thermal stabilization period. In various exemplary embodiments of the invention the thermal conductivity is calculated using the Stefan-Boltzmann law based on the thermal stabilization period and the differences in depths and steady state temperatures.

The method ends at 609.

As used herein the term "about" refers to ±10%.

The terms "comprises", "comprising", "includes", "including", "having" and their conjugates mean "including but not limited to".

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. Apparatus for identifying blood vessels in a thermal image of a section of a living body, the apparatus comprising:
a convolution unit, for convolving intensity data representing the thermal image with a predetermined vessel shapes filter thereby to provide filtered data;
a derivative calculator, for calculating, for each picture-element of said thermal image, calculating at least a first local derivative of said filtered data along a first dimension and a second local derivative of said filtered data along a second dimension, and selecting a highest of said first and said second local derivatives, thereby providing derivative data;
a local intensity extrema searcher, for searching in said derivative data for local intensity extrema; and
an interpolator, for applying an interpolation procedure for generating contours between at least a portion of said local intensity extrema, and identifying said contours as blood vessels.

2. The apparatus of claim 1, further comprising an intensity data inverter for inverting said intensity data by linear transformation.

3. The apparatus of claim 1, further comprising a masking unit for masking said intensity data so as to exclude at least a portion of said intensity data, said portion corresponding to picture-elements not belonging to blood vessels.

4. The apparatus of claim 3, wherein said masking unit is operable to calculate at least one of: local minimum, local maximum and local average for each picture-element of the thermal image.

5. The apparatus of claim 1, further comprising a normalization unit for normalizing said intensity data.

6. The apparatus of claim 1, further comprising a noise reduction unit which employs a noise removal procedure to exclude isolated local intensity extrema.

7. A method of identifying blood vessels in a thermal image of a section of a living body, the method comprising:
convolving intensity data representing the thermal image with a predetermined vessel shapes filter thereby providing filtered data;
for each picture-element of said thermal image, calculating at least a first local derivative of said filtered data along a first dimension and a second local derivative of said filtered data along a second dimension, and selecting a highest of said first and said second local derivatives, thereby providing derivative data;
searching in said derivative data for local intensity extrema; and
applying an interpolation procedure for generating contours between at least a portion of said local intensity extrema, and identifying said contours as blood vessels.

8. The method of claim 7, further comprising, prior to said convolution, inverting said intensity data by linear transformation.

9. The method of claim 7, further comprising masking said intensity data so as to exclude at least a portion of said intensity data, said portion corresponding to picture-elements not belonging to blood vessels.

10. The method of claim 9, wherein said masking comprises calculating at least one of: local minimum, local maximum and local average for each picture-element of the thermal image.

11. The method of claim 7, further comprising normalizing said intensity data.

12. The method of claim 7, further comprising, subsequently to said search for local intensity extrema, employing a noise reduction procedure for excluding isolated local intensity extrema.

13. The method of claim 7, further comprising generating a blood vessel map based on said identified blood vessels.

14. A method of recognizing an individual based on a body section of the individual, comprising:
identifying blood vessels in a thermal image of the body section using the method of claim 7, so as to generate a blood vessel map;
searching a searchable database of blood vessel maps for a map entry which is similar to said blood vessel map; and
identifying the individual based on said map entry.

15. A method of estimating characteristic heat conduction of a section of a living body, comprising:
obtaining a series of thermospatial representations describing the section of the living body while having at least two different shapes;
for each shape of said at least two different shapes, executing the method of claim 7 for identifying at least one blood vessel in thermal data of a respective thermospatial representation and calculating a depth of said at least one blood vessel;
determining thermal stabilization period for said at least one blood vessel; and
determining the characteristic heat conduction based at least in part on said thermal stabilization period.

* * * * *

UNITED STATES PATENT AND TRADEMARK OFFICE
CERTIFICATE OF CORRECTION

PATENT NO. : 9,144,397 B2  
APPLICATION NO. : 13/132332  
DATED : September 29, 2015  
INVENTOR(S) : Eyal Naimi et al.

Page 1 of 1

It is certified that error appears in the above-identified patent and that said Letters Patent is hereby corrected as shown below:

On the Title page, item (54) and in the Specification, column 1, line 2, in the Title, "THERMAL SIGNATURE" should be changed to --THERMOSPATIAL SIGNATURE--

Signed and Sealed this
Twenty-fourth Day of May, 2016

Michelle K. Lee
*Director of the United States Patent and Trademark Office*